(12) United States Patent
Wang et al.

(10) Patent No.: US 7,704,602 B2
(45) Date of Patent: Apr. 27, 2010

(54) IODINE/IODIDE-CONTAINING HOT MELT COATABLE ADHESIVE, METHODS AND USES THEREFOR

(75) Inventors: Danli Wang, Shoreview, MN (US); Stephen E. Krampe, Maplewood, MN (US); Zhiming Zhou, Woodbury, MN (US); Matthew T. Scholz, Woodbury, MN (US); Michael P. Daniels, Inver Grove Heights, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 78 days.

(21) Appl. No.: 11/672,694

(22) Filed: Feb. 8, 2007

(65) Prior Publication Data

US 2007/0142499 A1    Jun. 21, 2007

Related U.S. Application Data

(62) Division of application No. 11/116,465, filed on Apr. 28, 2005, now Pat. No. 7,189,793, which is a division of application No. 10/133,975, filed on Apr. 25, 2002, now Pat. No. 6,939,936.

(51) Int. Cl.
    *B32B 7/12* (2006.01)
    *C09J 4/00* (2006.01)

(52) U.S. Cl. .................... 428/346; 526/935; 156/331.6; 156/330.9; 156/327

(58) Field of Classification Search ................. 526/935; 156/331.6, 330.9, 327; 428/346
    See application file for complete search history.

(56) References Cited

U.S. PATENT DOCUMENTS

| | | | |
|---|---|---|---|
| 4,310,509 A | 1/1982 | Berglund et al. | |
| 4,323,557 A | 4/1982 | Rosso et al. | |
| 5,069,907 A | 12/1991 | Mixon et al. | |
| 5,242,985 A * | 9/1993 | Shih et al. | ................. 525/326.9 |
| 5,270,358 A | 12/1993 | Asmus | |
| 5,369,155 A | 11/1994 | Asmus | |
| 5,670,557 A | 9/1997 | Dietz et al. | |
| 5,674,561 A | 10/1997 | Dietz et al. | |
| 5,779,632 A | 7/1998 | Dietz et al. | |
| 5,803,086 A | 9/1998 | Scholz et al. | |
| 5,829,442 A | 11/1998 | Cox et al. | |
| 5,853,750 A | 12/1998 | Dietz et al. | |
| 5,952,398 A | 9/1999 | Dietz et al. | |
| 5,979,450 A | 11/1999 | Baker et al. | |
| 6,143,317 A | 11/2000 | Himmelsbach et al. | |
| 6,216,699 B1 | 4/2001 | Cox et al. | |

FOREIGN PATENT DOCUMENTS

| | | |
|---|---|---|
| WO | WO 95/20634 | 8/1995 |
| WO | WO 97/05171 | 2/1997 |
| WO | WO 00/56828 | 9/2000 |
| WO | WO 00/78885 | 12/2000 |

* cited by examiner

*Primary Examiner*—Thao T. Tran

(57) ABSTRACT

An iodine/iodide-containing hot melt coatable adhesive is provided. This adhesive is prepared by mixing iodine and an iodide salt, individually or in combination, with solubilizing liquids. The iodine and iodide salt are combined with a pre-adhesive composition in a hot melt mixer, with an iodine/iodide complexing agent being present in the mixture. The mixture is mixed at a temperature from about 130° C. to about 200° C. and sufficiently to form an iodine/iodide-containing hot melt coatable adhesive. Alternatively, the iodide may be generated in situ. The adhesive so prepared may be packaged for coating on a substrate at a later time, or may be immediately coated to form an adhesive composite. Adhesive composites, particularly surgical incise drapes, are provided incorporating this hot melt coatable adhesive.

22 Claims, No Drawings

IODINE/IODIDE-CONTAINING HOT MELT COATABLE ADHESIVE, METHODS AND USES THEREFOR

CROSS REFERENCE TO RELATED APPLICATIONS

This application is a division of U.S. patent application Ser. No. 11/116,465, filed Apr. 28, 2005 (now U.S. Pat. No. 7,189,793) which is a division of U.S. patent application Ser. No. 10/133,975, filed Apr. 25, 2002, (now U.S. Pat. No. 6,939,936).

FIELD OF THE INVENTION

The present invention relates to hot melt coatable adhesives. More specifically, the present invention relates to hot melt coatable adhesives having iodine/iodide-contained therein.

BACKGROUND OF THE INVENTION

Rigorous adherence to the principles of asepsis is the foundation of surgical site infection prevention. It is critical to minimize exposure of the wound to bacterial contamination from bacteria on the patient's skin, members of the surgical team, and from non-sterile equipment in the operating room through the use of gloves, gowns, masks, and drapes. Draping of the surgical site provides a sterile work surface and helps minimize the transfer of microorganisms between non-sterile areas and the surgical wound. These measures also may help protect health care professionals from exposure to pathogens in the patient's blood and other body fluids. To help prevent surgical site infection, it is critical to reduce and restrict microorganisms from entering the open surgical wound. Incise drapes, such as Steri-Drape™ drape and Ioban™ 2 Antimicrobial Skin Prepping System from 3M, provide a sterile surface to the wound edge during surgery. The film adheres securely to wound edges, which is critical in maintaining the barrier to skin flora. Some incise drapes such as Ioban™ 2 contain an antimicrobial agent, preferably iodophor, in the adhesive so that the drape itself provides antimicrobial activity.

A pressure sensitive adhesive having a broad spectrum antimicrobial contained therein is disclosed in U.S. Pat. No. 4,310,509. When the adhesive composition is placed in contact with the skin, it uniformly and controllably releases the broad spectrum antimicrobial agent. The process as described therein involves forming an emulsifiable concentrate or an organic solution concentrate of the broad spectrum antimicrobial and mixing it into the adhesive such that the broad spectrum antimicrobial is homogeneously dispersed as a separate phase throughout the adhesive medium. U.S. Pat. No. 4,323,557 discloses pressure sensitive adhesives that are stable complexes of iodine, an iodide ion and a dermatologically acceptable normally room temperature tacky pressure sensitive adhesive.

Solventless hot melt adhesive compositions containing a specific antimicrobial agent, diiodomethyl-p-tolylsulfone, are described in U.S. Pat. Nos. 6,216,699 and 5,829,422. This compound is stated to be a heat stable antimicrobial agent at column five, lines 47-56 (in the '699 patent). The addition of this heat stable antimicrobial agent to the adhesive composition is stated to provide an effective antimicrobial adhesive which retains desirable properties during use and application even after the adhesive has been processed at temperatures in the range of 275° F. to 350° F.

PCT publications WO 00/56828 and WO 00/78885 describe wet stick pressure sensitive adhesives comprising the polymerization product of defined monomers, wherein the pressure sensitive adhesive adheres to wet surface substrates. These adhesives may be made by a hot melt coating process, and additionally may be used in conjunction with surgical drapes. These references do not disclose the incorporation of antimicrobial agents in the adhesive.

U.S. Pat. No. 5,369,155 discloses a composite of gel of swollen hydrocolloid dispersed in a pressure sensitive adhesive matrix. The gel-adhesive composite may be used with surgical incise drapes, and may optionally incorporate antimicrobial agents. A list of optional antimicrobial agents is provided at column 12, lines 32-39, which includes iodine and iodophors. In the examples, the composite is coated from a solvent onto a release liner and laminated to a backing.

Active substance plasters are described in U.S. Pat. No. 6,143,317. These plasters comprise a backing material having a foamed hot melt adhesive composition comprising an active substance. The list of active substances that may be incorporated in the foamed hot melt adhesive includes iodine, but there is no disclosure of how such an iodine would be incorporated, and no disclosure of the complexing agent for iodine and iodide ion compositions.

SUMMARY OF THE INVENTION

A method of making an iodine/iodide-containing hot melt coatable adhesive is provided by the present invention. In this method, iodine is mixed with an iodine solubilizing liquid to form an iodine composition, an iodide salt is mixed with an iodide solubilizing liquid to form an iodide composition, and a pre-adhesive composition is provided. The iodine composition, iodide composition and pre-adhesive composition are mixed in a hot melt mixer to form a mixture, with an iodine/iodide complexing agent being present in the mixture. The mixing is carried out at a temperature from about 130° C. to about 200° C., and with sufficient mixing to form an iodine/iodide-complex-containing, hot melt coatable adhesive. The adhesive so prepared may be packaged for coating on a substrate at a later time, or may be immediately coated to form an adhesive composite. Adhesive composites, particularly surgical incise drapes, are provided incorporating hot melt coatable adhesives of this invention.

In an alternative embodiment, the iodide ion may be formed in-situ from iodine by reaction with a suitable reducing agent. The reducing agent may be provided in the iodine solubilizing liquid, in the pre-adhesive mixture, or as a separate component to be added at the time of mixing or in a post-mixing process. Thus, the reaction of iodine with the reducing agent may occur in the solubilizing liquid, in the hot melt mixer/extruder, or post mixing/extruding or some combination thereof.

DETAILED DESCRIPTION OF THE PREFERRED EMBODIMENTS

Iodine has a relatively high vapor pressure. It is well known, for example, that iodine will sublime at room temperature. For example, the vapor pressure is reported to be 0.30 mmHG at 25 C, 26.7 mmHg at 90 C and boils at 184.4 C (thus having a vapor pressure of 760 mmHg at 184.4 C) (Merck Index $12^{th}$ Ed). For this reason, previous methods for preparing adhesives containing iodine have utilized only mild processing steps to avoid loss of iodine. Therefore, it is very surprising that it is possible to hot melt coat an adhesive containing iodine at temperatures over 130° C. without significant loss of iodine. Further, it has surprisingly been discovered that iodine and iodide ions can be effectively incorporated in a hot melt coatable adhesive in a manner that will provide antimicrobial activity.

Hot melt adhesives provide a number of significant advantages as compared to solvent based or water-based adhesives. Because the hot melt adhesive contains only the material that is used in the adhesive without excess water or solvent, it is far easier and less expensive to transport than solvent based or water-based adhesives. This means that the hot melt adhesive may be formulated in one location and easily transported to another location for coating to form the adhesive composite. This transportability makes it possible to have a uniform adhesive composition in a product line on a global basis, provides efficiencies and economies of scale with respect to supply of individual ingredients of the adhesive composition, and enables the ability to use local low-cost manufacturing operations.

Hot melt adhesives are also preferred over solvent based or water-based adhesives because they are less expensive to process. Hot melt adhesives contain no solvent, and thus there is no cost of the solvent itself, or of removing and possibly recovering the solvent. Furthermore, hot melt adhesives present significantly fewer pollution emission issues. Because the hot melt adhesive contains no extraneous liquid, the coating process does not require the step of drying the coated adhesive to remove liquid. This results in significant cost savings in both energy and avoiding the need to install expensive solvent capture equipment.

Iodine and/or some of its ionic species are in some environments highly corrosive to certain metals. It has surprisingly been found that the process for making the hot melt coatable adhesive compositions of the present invention does not result in the corrosion or deterioration of the extruders employed. Thus, even mixing and extrusion equipment made from ordinary tool steel surprisingly has not been adversely affected when used in preparing the hot melt coatable adhesive in accordance with the process described herein.

Complexes of hydrogen triiodide with polyvinylpyrrrolidone have been reported to comprise hydrogen bond, ionic, and perhaps hydrogen bond and ionic associations. While most of these associations have been reported as intra-chain polymer associations, inter-chain associations are also possible. Inter-chain associations/complexes could be expected to crosslink the polymer network. Crosslinked or coordinated polymeric systems generally lead to significant problems in extrusion processes due to the expectation that such systems would not flow through the extruder. Therefore, it is particularly surprising that an ionic complex, such as is formed when iodine and iodide complex with the complexing agent, could be utilized in a hot melt process.

By "hot melt coatable adhesive" is meant a composition that may be coated on a substrate while in the molten state, which composition after coating may be used to adhere one article to another. Preferably, the hot melt coatable adhesive is a pressure sensitive adhesive at room temperature (i.e. at about 21° C.). For purposes of the present invention, "pressure sensitive adhesive" or "PSA" refers to a viscoelastic material that displays tackiness and adheres well to a wide variety of substrates after applying only light pressure (e.g., finger pressure). One well known means of identifying pressure sensitive adhesives is the Dahlquist criterion. This criterion defines a pressure sensitive adhesive as an adhesive having a 1 second creep compliance of greater than $1 \times 10^{-6}$ cm$^2$/dyne as described in *Handbook of Pressure Sensitive Adhesive Technology*, Donatas Satas (Ed.), $2^{nd}$ Edition, p. 172, Van Nostrand Reinhold, New York, N.Y., 1989;

The iodide as described herein is an ion provided in the form of salt, together with any appropriate counter ion for incorporation in the adhesives of the present invention. For example, sodium iodide, potassium iodide, lithium iodide, hydrogen iodide, ammonium iodide and quaternary amine-iodide salts are contemplated. Sodium iodide, potassium iodide, and hydrogen iodide are particularly preferred iodide salts for use in the present invention.

In one embodiment of the process of the present invention, iodine is mixed with an iodine solubilizing liquid to form an iodine composition, and an iodide salt is mixed with an iodide salt solubilizing liquid to form an iodide composition. As used herein, the term "liquid" refers to compounds that are liquids (i.e. pourable) at temperatures less than 100° C. Preferably these compounds are liquids at temperatures less than 50° C., more preferably less than 30° C. and most preferably at less than 25° C. The solubilizing liquid for each of the iodine and iodide components is present in an amount effective to dissolve solid components either prior to or during the mixing of these components in the ultimate adhesive composition, such that iodine or iodide particles of substantial size are not present in the ultimate hot melt adhesive composition. Thus, while the iodine or iodide may be introduced in the mixer in the form of, for example, a paste that contains some insoluble iodine or iodide particles, sufficient solubilizing liquid is present to facilitate solubilizing of the iodine or iodide particles under the conditions of mixing to avoid the presence of insoluble particles of substantial size at the time of coating of the hot melt coatable adhesive. The presence of insoluble particles of substantial size is not tolerable in the hot melt coating process, because such particles cause interference or even stop the flow of the hot melt adhesive as the adhesive passes through filters commonly found in a hot melt coater. Even if the filter was removed, particles can become lodged in the coating die, interfering with the coating process and leading to coating inconsistency. The optional presence of small particles that do not cause such interference is contemplated in the present compositions.

Preferably, the iodine and iodide salt are each solubilized, i.e. the iodine and iodide salts are in solution such that there are no insoluble particles of substantial size present in the iodine and iodide compositions. In a preferred embodiment of the present invention, the iodine and iodide are solubilized together as a single composition.

In an alternative preferred embodiment, the iodine composition and the iodide composition are provided as separate compositions. A preferred version of this embodiment is when the iodine solubilizing liquid and the iodide salt solubilizing liquid are the same. This provides for reduction in the number of raw materials, and assures complete mixability of the iodine solution with the iodide solution. In a more preferred embodiment, the iodine and iodide salt are mixed together as a single composition. This embodiment reduces the number of components to be added in the manufacturing facility to the adhesive mixture in the manufacturing process, thereby simplifying the actual adhesive assembly. Simplification in this manner is desirable, because it reduces the number of components that must be handled on the manufacturing floor, and also reduces the chances of error in addition of components in the manufacturing process.

In another embodiment of the present invention, the iodide ion is formed in an in-situ from iodine using a suitable reducing agent. Preferably, the reducing agent is non-toxic. For example, addition of reducing agents such as thiosulfate salts, bisulfite salts and the like can convert a portion of the iodine to iodide. This reducing agent may be provided in the iodine solubilizing liquid, in the preadhesive mixture, or as a separate stream. The reaction of iodine with the reducing agent thus may occur in the solubilizing liquid, in the hot melt mixer/extruder, or post mixing/extruding or a combination thereof In this embodiment, an iodide solubilizing liquid is provided so that the liquid is available at the time of generation of the iodide.

The solubilizing liquid for either the iodine or the iodide may be a single liquid or a blend of liquids. The solubilizing liquids may be a mere temporary carrier that is removed from the composition during or after the mixing process, or may remain in the final hot melt coatable adhesive composition. The solubilizing liquids may optionally perform a separate function in the final hot melt coatable adhesive composition, such as a plasticizing function, a reactive function where the solubilizing liquid reacts with other components to form part of the adhesive matrix, a cosmetic function such as a fragrance, or as a complexing agent for the iodine/iodide as discussed more completely below.

In one embodiment of the present invention, the iodine and the iodide ion are mixed with solubilizing liquids that do not act as a complexing agent for the iodine/iodide.

In a preferred embodiment of the present invention, solubilizing liquids are selected from the group consisting of water and a non-polymerizable organic solvent. The organic solvent may be volatile or nonvolatile. Examples of volatile non-polymerizable organic solvents include C1-C10 alcohols such as ethanol, isopropanol, n-propanol, phenoxyethanol and butanol; C3-C6 ketones such as acetone and methylethylketone; C2-C8 esters such as methyl acetate; C2-C8 ethers such as tetrahydrofuran, amides such as N-methylpyrolidone, dimethylforamide, dimethylacetamide, and lactones such as butyrolactone; esters, such as ethyl acetate and butyl acetate; ketones, such as acetone and methylethyl ketone; and aromatics organic solvents, such as toluene and xylene.

The solubilizing liquids may alternatively be selected from non-volatile organic solvents. For purposes of the present invention, an organic solvent is considered to be nonvolatile if greater than 80% of the solvent remains in the adhesive composition throughout the mixing and hot melt coating processes. Because these solvents remain in the hot melt coatable adhesive composition, they function as plasticizers, generally lowering the glass transition temperature of the composition. Some of these plasticizers may complex with the iodine/iodide as a complexing agent, further discussed below, while others may simply dissolve these components.

Examples of nonvolatile organic plasticizers include compounds containing one or more hydroxyl groups, and particularly glycols such glycerin; 1,2 pentanediol; 2,4 diethyl-1,5 pentanediol; 2-methyl-1,3-propanediol; as well as monofunctional compounds such 3-methoxy-methylbutanol ("MMB"). Additional examples of nonvolatile organic plasticizers include polyethers, including polyethoxylated phenols such as Pycal 94 (phenoxypolyethyleneglycol); alkyl, aryl, and aralkyl ether glycols such as those sold under the Dowanol™ tradename by Dow Chemical, Midland Mich. including but not limited to propyelene glycolmonobutyl ether (Dowanol PnB, tripropyleneglycol monobutyl ether (Dowanol TPnB), dipropyeleneglycol monobutyl ether (Dowanol DPnB), propylene glycol monophenyl ether (Dowanol PPH), propylene glycol monomethyl ether (Dowanol PM); polyethoxylated alkyl phenols such as Triton X35 and Trion X102; mono or polysubstituted polyethylene glycols such as PEG 400 diethylhexanoate (TegMer 809, CP Hall), PEG 400 monolaurate (CHP-30N available from CP Hall) and PEG 400 monooleate (CPH-41N available from CPHall); amides such as higher alkyl substituted N-alkyl pyrrolidones such as N-octylpyrrolidone; sulfonamides such as N-butylbenzene sulfonamide (available from CP Hall), benzoate esters such as those available from Velsicol Chemical Corp., Rosemont Ill. under the Benzoflex tradename including dipropylene glycoldibenzoate (Benzoflex 50), diethylene glycol dibenzoate, benzoic acid diester of 2,2,4 trimethyl 1,3 pentane diol (Benzoflex 354), ethylene glycol dibenzoate, tetraetheylene glycoldibenzoate, and the like; polyethylene glycols and ethylene oxide propylene oxide random and block copolymers having a molecular weight less than 10,000 daltons preferably less than about 5000 daltons, more preferably less than about 2500 daltons; and combinations thereof. As used herein the term polyethylene glycols refers to glycols having 2-6 alcohol groups that have been reacted with ethylene oxide or a 2 haloethanol. Preferred polyethylene glycols are formed from ethylene glycol, propylene glycol, glycerin, trimethylolpropane, pentaerithritol, sucrose and the like. Most preferred polyethylene glycols are formed from ethylene glycol, propylene glycol, glycerin, and trimethylolpropane. Polyalkylene glycols such as polypropylene glycol, polytetramethylene glycol, or random or block copolymers of C2-C4 alkylene oxide groups may also be selected as the plasticizer. Polyethylene glycols and derivatives thereof are presently preferred. It is important that the plasticizers be compatible with the pressure sensitive adhesive polymer. For example, it is presently preferred to use non-volatile non-polymerizable plasticizers that have less than 2 nucleophilic groups such as hydroxyl groups when blended with polymers having acid functionality, since compounds having more than two nucleophilic groups may result in crosslinking of the adhesive in the hot melt extruder at the high extrusion temperatures. Importantly the non-volatile plasticizers preferably form a homogeneous solution with the hot melt coatable adhesive polymer in the hot melt extruder, with the adhesive remaining a homogeneous composition upon cooling, such that the extruded hot melt coatable adhesive composition is uniform in iodine concentration.

A list of some preferred plasticizer compounds appears below. Note that all of these compounds are capable of dissolving 6% iodine/7.2% iodide with mild warming.

| Trade Name | | 5% PVPI(*) | 2% I$_2$/2.4% NaI | 18% I$_2$ |
| --- | --- | --- | --- | --- |
| Pycal 94 | (phenoxypolyethyleneglycol) | Soluble | Soluble | soluble |
| Plasthall BSA | N-n-butylbenzenesulfonamide | Soluble after heating to 70° C. | Soluble | Soluble |
| TerMerR 804 | tetraethyleneglycol di-2ethylhexanoate | Not Soluble | Soluble | Soluble |
| TegMerR 809 | PEG400 di-2ethylhexanoate | Not Soluble | Soluble | Soluble |
| CPH-30N | PEG400 monolaurate | Not Soluble | Soluble | Soluble |
| CPH-41N | PEG400 monooleate | Not Soluble | Soluble | Soluble |

*PVPI = povidone-iodine USP.

Optionally, other iodine species may also be present in the iodine and/or iodide compositions, or in the ultimate adhesive. For example, iodate ($IO_3^-$) may also be added to the adhesive to improve stability if desired. Iodate ion has been reported to improve stability of aqueous iodine compositions.

Another embodiment of the present invention is where the solubilizing liquid is polymerizable. Examples of such polymerizable solubilizing liquids include vinylic monomers comprising polyethylene glycol chains terminated in either an alcohol or an alkyl ether or ester such as monoethylenically unsaturated poly(alkylene oxide) (meth)acrylic monomer having the formula:

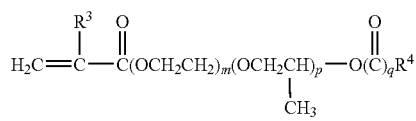

wherein: m is at least 2; p is 0 to 50; q is 0 or 1; $R^3$ is H or $CH_3$; and $R^4$ is hydrogen or linear or branched alkyl and/or aryl groups; with the proviso that the isopropylene oxide groups (the "p" groups) and the ethylene oxide groups (the "m" groups) are arranged in a reversed, alternating, random, or block configuration. Other useful polymerizable organic solvents include phenoxyethyl acrylate, benzyl acrylate, N-vinyl pyrrolidone, N-vinylcaprolactam, pyrrolidone ethylacrylate, and the like. Preferably, polymerizable solubilizing liquids are utilized in a manner that limits potential premature or undesired reaction, for example, with iodine.

Particularly preferred embodiments of the present invention are where the iodine solubilizing liquid and the iodide solubilizing liquid are selected from the group consisting of water and a non-reactive organic solvent. More particularly preferred embodiments are wherein the iodine solubilizing liquid is selected from an organic solvent having hydroxyl group functionality (e.g. a glycol) and the iodide solubilizing liquid is water. Where the iodine solubilizing liquid and the iodide solubilizing liquid are different liquids, they are preferably proportionally added into the hotmelt extruder simultaneously, with the iodine and the iodide forming the iodine/iodide complex in the hotmelt polymer. This embodiment provides particular benefit, because the solubilizing liquid may be selected to match high solubility of the iodide or the iodide in the particular solubilizing liquid. Thus, for example, iodine is much more soluble in many glycols than the iodide, and iodide is much more soluble in water than the iodine. By selection of the solubilizing fluids to match with the particular species to be solubilized, the amount of liquid to be added into the extruder may be minimized.

The iodine solution and/or iodide solution (which includes iodine/iodide combination solutions, if both are combined) may be formulated to be a liquid, solid, or a paste at room temperature (e.g. at about 23° C.), provided that homogeneous mixing of the iodine and iodide in the hot melt coatable adhesive is possible. With solid compositions, the mixture may be heated to above the melting point and pumped into the hot melt extruder. Preferably the iodine and iodide salt are completely solubilized in the solubilizing liquid to form a homogenous solution at or above the coating temperature. More preferably the iodine and iodide salt are soluble in the solubilizing liquid at temperatures well below the coating temperature and most preferably they are soluble in the solubilizing liquid at room temperature (23° C.). This greatly facilitates introduction of the iodine/iodide material into the hot melt coater. Alternatively, the solubilized components may be combined with additional ingredients to form a solid suitable for introduction into the hot melt coater such as pellets, flakes, granules, or powder.

In another embodiment of the present invention, the iodine and the iodide ion are solubilized in a solubilizing liquid that does act as a complexing agent for the iodine/iodide. Such complexing agents are discussed in more detail below. Alternatively, the solubilizing liquid may be a mixture of both a complexing agent and a material that does not complex the iodine/iodide mixture. This embodiment provides a complex of iodine and iodide that is formed prior to mixing with the pre-adhesive composition, with little or no loss of iodine in the form of a gas.

For purposes of the present invention, an iodine/iodide complexing agent is a material that associates with molecules of iodine and iodide ions, thereby forming an iodophor. As used herein, an iodophor is a complex of iodine/iodide with a complexing agent, wherein a portion of the elemental iodine molecules are in equilibrium with, but not bound to, the complexing agent. These molecules are termed "free" iodine and are believed to be responsible for the germicidal action of this complex. As germs are killed, some of the "free" iodine is depleted and replaced with iodine that is liberated from the complex.

As discussed above, the complexing agent may be a component of the solubilizing liquid. Alternatively or in addition, the complexing agent may be added to the pre-adhesive formulation as a separate ingredient, or may be provided as a functionality on a molecule or polymer carrying out a separate function as part of the pre-adhesive composition. For example, the complexing agent may be an adhesive polymer that contains a functionality that interacts with iodine and iodide to form an iodophor.

Preferably, the iodine/iodide complexing agent comprises a compound capable of forming iodophors, wherein the compound contains hydroxyl functionality, lactam functionality, amide functional groups, amine oxide functional groups, or polyether functionality.

Preferred iodine/iodide complexing agents include glycol compounds and compounds containing plural hydroxyl functionalities, such as glycol monomers; polyethylene glycol (PEG) compounds such as PEG side chain (meth)acrylate and PEG esters; and polymers containing lactam functionality, such as N-vinylpyrrolidone, N-vinylcaprolactam, pyrrolidone ethylacrylate, polyvinylpyrrolidone, polyvinyl caprolactam, and n-octyl pyrrolidone. Preferred glycols include both polyhydroxyfunctional compounds such as glycerin, propylene glycol and 2 methyl 1,3 propanediol as well as monohydroxyfunctional compounds such as Pycal 94 (phenoxypolyethyleneglycol), 3-methoxy methylbutanol ("MMB"), 2 phenoxyethanol and the like. Among these compounds, Pycal 94 is preferred. Additionally, iodine/iodide complexing agents may be polymers or oligomers having amide functional groups such as polyvinylpyrrolidone. Other iodine/iodide complexing agents are copolymers of moieties having complexing functionality, such as those derived at least in part from N-vinyl lactams, pyrrolidone alkylacrylates, and acrylamides; with other unsaturated monomers such as, but not limited to, acrylates, methacrylates, and acrylamides. Preferred examples of such copolymers are disclosed in U.S. Patent Publication No. 2003/0113365-A1 (Schaberg, et.al.). Other preferred polymers include various polyether glycols including polyether-containing surfactants such as nonylphenolethoxylates octylphenolethoxylates and the like; polyvinyl alcohols; polycarboxylic acids such as polyacrylic acid; polysaccharides such as dextrose, and the like; and combinations thereof. Preferred iodine/iodide complexing agents include polymers comprising amide functionality, including but not limited to polymers derived from N-vinyl lactams, polyethoxylated compounds and vinylic polymers comprising polyethoxylated groups.

A pre-adhesive composition to be used in the present invention is a polymeric resin composition that is coatable by a hot melt process, the components of which are selected to provide the desired adhesive properties of the ultimate adhesive composite. Preferably, the pre-adhesive composition is formulated such that, after incorporation of other components and coating on a substrate, it will provide a pressure sensitive adhesive.

Examples of pre-adhesive compositions useful in the present invention include, for example, those based on natural rubbers, synthetic rubbers, styrene block copolymers including but not limited to Styrene-Isoprene-Styrene (SIS), styrene-butadiene, styrene-isoprene and derivatives thereof such as those available from Kraton Polymers under the Kraton tradename, polyvinyl ethers, poly (meth)acrylates (including both acrylates and methacrylates), polyolefins such as poly-alpha olefins, silicones, and blends or mixtures thereof. Particularly preferred adhesive compositions are based on poly (meth)acrylates (including both acrylates and methacrylates). The polyacrylates may also comprise other vinylic non-acrylate monomers such as but not limited to N-vinyl lactams, (meth)acrylamides, styrene, methylvinyl ether, polystyrene macromers, vinyl acetate and the like. Additionally, in certain embodiments of the present invention, fully hydrogenated adhesives may be preferred to prevent addition of iodine to any unsaturated functionalities present in the composition.

The adhesive composition may be made from a formulation of polymers that is inherently tacky. If desired, tackifiers may be added to a base polymeric formulation to form the pressure sensitive adhesive. Useful tackifiers include, for example, rosin ester resins, aromatic hydrocarbon resins, aliphatic hydrocarbon resins, and terpene resins.

Other materials can be added for special purposes, including, for example, oils, plasticizers, antioxidants, ultraviolet ("UV") stabilizers, hydrogenated butyl rubber, pigments, dyes, hydrocolloid particles such as those used in bioadhesive compositions and wound dressings disclosed in U.S. Pat. No. 5,750,134 and U.S. Pat. No. 5,633,010, additional antimicrobial agents, antioxidants and curing agents.

Examples of antimicrobial agents that may optionally be incorporated in addition to iodine include alpha hydroxyacids such as but not limited to lactic acid, malic acid, citric acid, 2-hydroxybutanoic acid, 3-hydroxybutanoic acid, mandelic acid, gluconic acid, tartaric acid, salicylic acid, as well as derivatives thereof (e.g., compounds substituted with hydroxyls, phenyl groups, hydroxyphenyl groups, alkyl groups, halogens, as well as combinations thereof), C8-C18 fatty acids, C8-C18 sulfonic acids and there salts, quaternary ammonium surfactants having at least one alkyl chain of at least 8 carbon atoms or a benzyl group, parachlorometaxylenol (PCMX), triclosan, hexachlorophene, fatty acid monoesters of glycerin and propylene glycol such as glycerol monolaurate, glycerol monocaprylate, glycerol monocaprate, propylene glycol monolaurate, propylene glycol monocaprylate, propylene glycol moncaprate, phenols, surfactants and polymers that include a (C12-C22)hydrophobe and a quaternary ammonium group, polyquaternary amines such as polyhexamethylene biguanide, quaternary silanes, silver, silver salts such as silver chloride, silver oxide and silver sulfadiazine, methyl, ethyl, propyl and butyl parabens, octenidene, and the like, as well as combinations thereof.

The adhesive composition is preferably prepared by at least partially polymerizing a pre-adhesive composition comprising a monomeric mixture or a prepolymeric mixture to form a hot melt adhesive. Preferably, the pre-adhesive composition can be polymerized to form a pressure sensitive hot melt adhesive composition.

The pre-adhesive composition is preferably polymerized by substantially solventless polymerization methods, such as the continuous free radical polymerization method described in U.S. Pat. Nos. 4,619,979 and 4,843,134; the essentially adiabatic polymerization methods using a batch reactor described in U.S. Pat. No. 5,637,646; and, the methods described for polymerizing packaged polymerizable mixtures described in U.S. Pat. No. 5,804,610 may also be utilized to prepare the polymers.

A small amount of volatile, non-polymerizable solvent may be included in the pre-adhesive composition to dissolve other additives, such as a crosslinking agent. The pre-adhesive composition preferably contains less than 10 weight percent of solvent. In a preferred embodiment, the pre-adhesive composition contains less than 5 weight percent of solvent, and in another preferred embodiment, the pre-adhesive composition contains less than 1 weight percent of solvent. In a preferred embodiment, the pre-adhesive composition is essentially free of solvent. As used herein the term "solventless" refers to hot melt adhesives that are not required to undergo a solvent removal process after coating. These solventless adhesives are generally coated by an extrusion process at elevated temperatures to yield a composition having less than 5% by weight volatile organics. Total volatile organics can be determined by heating the coated composition having a thickness of less than 125 microns to 100° C. at 1atm pressure for 30 min. These adhesives should not lose more than 5 weight percent of their total weight in this evaluation.

Depending upon the method of polymerization, the pre-adhesive composition may include an appropriate initiator. For polymerization by ultraviolet or visible light, an appropriate photoinitiator is included. For thermal polymerization, a thermal initiator is included. For free radical polymerization, an appropriate free radical initiator, such as a peroxide initiator, a persulfate initiator, azo initiators such as those available under the Vazo tradename, available from DuPont, or a redox (oxidation-reduction) initiator is provided. A combination of different initiator systems, such as a combination of thermal and photoinitiation may also be used to prepare compositions according to the invention. For example, the pre-adhesive compositions may polymerized, e.g., in a reactive extruder, to a certain conversion using a thermal initiator, the resulting composition (still in a pre-adhesive state) combined with packaging material (e.g., in the form of a pouch or shell) and a photoinitiator, and the polymerization completed upon exposure to ultraviolet radiation. Conversely, the initial polymerization may be initiated by a photoinitiator, and the polymerization subsequently completed using a thermal initiator. The thermal initiator and photoinitiator may also be used together, rather than being added sequentially.

Optionally, the pre-adhesive composition also includes a chain transfer agent to control the molecular weight of the polymer. Chain transfer agents are materials that regulate free radical polymerization and are generally known in the art. Suitable chain transfer agents include halogenated hydrocarbons such as carbon tetrabromide; sulfur compounds such as hexyl mercaptan, lauryl mercaptan, butyl mercaptan, ethanethiol, tert-dodecyl mercaptan, sec-dodecyl mercaptan, n-dodecyl mercaptan, isooctylthioglycolate (IOTG), 2-ethylhexyl thioglycolate, 2-ethylhexyl mercaptopropionate, 2-mercaptoimidazole, and 2-mercaptoethyl ether; and solvents such as ethanol, isopropanol, and ethyl acetate. The amount of chain transfer agent that is useful depends upon the desired molecular weight and the type of chain transfer agent. The chain transfer agent, if present, is typically used in amounts from about 0.001 part to about 10 parts by weight per 100 parts of total monomer, and preferably from about 0.01 part to about 0.5 part, and most preferably from about 0.02 part to about 0.20 part.

The pre-adhesive composition may further comprise an effective amount of a crosslinking agent that may be activated after the adhesive has been hot melt coated. The crosslinking agent can be added to the polymerized adhesive before or during hot melt coating, or it can be added to the pre-adhesive composition. When added to the pre-adhesive composition, the crosslinking agent can remain intact as a separate species in the adhesive, or it can be co-polymerized with the monomers. Crosslinking is preferably initiated after hot melt coating, and the crosslinking is preferably initiated by ultraviolet radiation, or ionizing radiation such as gamma radiation or electron beam (the use of separate crosslinking agents being optional in the case of ionizing radiation).

Acrylate copolymers can be crosslinked by exposure to ultraviolet radiation from, for example, medium pressure mercury arc lamps. It is preferred that crosslinking agents activated by ultraviolet radiation be primarily activated by a different wavelength of energy than that used for the polymerization. For example, low intensity black lights may be used for polymerization and mercury arc lamps may be used for the subsequent crosslinking.

In some cases, polymers may be dissolved in the monomers before polymerization to modify the adhesive characteristics, or to make a syrup or monomeric mixture. Examples of such polymers include silicone pressure sensitive adhesives, acrylic polymers and copolymers, ethylene-vinyl acetate copolymers, acrylonitrile copolymers, and co-polymerizable macromers such as those described in U.S. Pat. No. 4,554,324 (Husman et al.).

Other additives can be included in the pre-adhesive composition, or added at the time of hot melt coating to change the properties of the adhesive. Such additives, or fillers, include plasticizers, pigments, glass or polymeric bubbles or beads (which may be expanded or unexpanded), fibers, reinforcing agents, hydrophobic or hydrophilic silica, calcium carbonate, toughening agents, fire retardants, antioxidants, finely ground polymeric particles such as polyester, nylon, and polypropylene, additional antimicrobial agents and stabilizers. The additives are added in amounts sufficient to obtain the desired end properties.

In a preferred embodiment, the pressure sensitive adhesive is based on at least one poly(meth)acrylate (e.g. is a (meth) acrylic pressure sensitive adhesive). Poly(meth)acrylic pressure sensitive adhesives are preferably derived from, for example, at least one alkyl (meth)acrylate ester monomer such as, for example, isooctyl acrylate, isononyl acrylate, 2-methyl-butyl acrylate, 2-ethyl-hexyl acrylate and n-butyl acrylate; and at least one optional co-monomer component such as, for example, (meth)acrylic acid, vinyl acetate, N-vinyl pyrrolidone, (meth)acrylamide, a vinyl ester, a fumarate, a styrene macromer, or combinations thereof. Preferably, the poly(meth)acrylic pressure sensitive adhesive polymer is derived from between about 0 and about 20 weight percent of acrylic acid and between about 100 and about 80 weight percent of at least one of isooctyl acrylate, 2-ethyl-hexyl acrylate or n-butyl acrylate composition, preferably isooctyl acrylate. A preferred pressure sensitive adhesive (PSA) polymer embodiment for the present invention is derived from between about 2 and about 10 weight percent acrylic acid and between about 90 and about 98 weight percent of at least one of isooctyl acrylate, 2-ethyl-hexyl acrylate or n-butyl acrylate composition. One specific PSA polymer embodiment for the present invention is derived from about 2 weight percent to about 10 weight percent acrylic acid, about 90 weight percent to about 98 weight percent of isooctyl acrylate, and about 2 weight percent to about 6 weight percent styrene macromer. In a separate preferred embodiment, the adhesive polymer is comprise of about 85-98% isooctyl acrylate, 2-ethyl-hexyl acrylate or n-butyl acrylate or a combination thereof and 2-15% of a N-vinyl lactam such as N-vinylpyrrolidone, N-vinylcaprolactam, or pyrrolidone ethylacrylate. Preferably the PSA polymer is comprised of about 90-98% isooctyl acrylate, 2-ethyl-hexyl acrylate or n-butyl acrylate or a combination thereof and 2-10% of a N-vinyl lactam such as N-vinylpyrrolidone, N-vinylcaprolactam, or pyrrolidone ethylacrylate. In yet another preferred embodiment of the present invention the PSA polymer is derived from between about 35 and about 55 weight percent acrylic acid and between about 35 and about 55 weight percent of at least one of isooctyl acrylate, 2-ethyl-hexyl acrylate or n-butyl and between about 2 and about 10 percent by weight of at least one N-vinylpyrrolidone, N-vinylcaprolactam, and pyrrolidone ethylacrylate.

A particularly preferred embodiment of the present invention utilizes a hot melt coatable adhesive composition that results in an ultimate adhesive composite that provides good adhesion to wet surfaces. Wet surface adhesion is particularly important in the environment of medical applications, and particularly for wound dressings and surgical incise drapes. These applications provide extreme challenges to adhesion of the adhesive composite, because excess fluid may gather at the wound site, or as a result of the surgical procedure. Additionally, the use of such adhesive composites in certain hot and humid environments present specific adhesive challenges due to the presence of fluid. PSAs that adhere to wet or moist surfaces, particularly wet skin, are referred to as "wet-stick" adhesives.

A particularly preferred embodiment of the present invention comprises an adhesive composition comprising the solventless polymerization product of:

(a) about 30 to about 70 parts by weight of an (meth) acrylate ester monomer wherein the (meth)acrylate ester monomer, when homopolymerized, has a Tg of less than about 10° C.;

(b) about 70 to about 30 parts by weight of a hydrophilic acidic ethylenically unsaturated comonomer; and (c) about 10 to 100 parts based on 100 parts of the sum of components (a)+(b) of a non-reactive plasticizing agent, wherein the pressure sensitive adhesive adheres to wet substrate surfaces. This adhesive is described in WO 00/56828.

In another particularly preferred embodiment, the adhesive composition is a pressure-sensitive adhesive comprising:

(a) a pressure-sensitive acrylate adhesive comprising:
  (i) at least one copolymerized monoethylenically unsaturated (meth)acrylic acid ester comprising an alkyl group having at least 4 carbons on average that, when homopolymerized, preferably has a glass transition temperature of less than about 10° C.; and
  (ii) at least one copolymerized monoethylenically unsaturated reinforcing monomer that, when homopolymerized, preferably has a glass transition temperature of at least about 10° C.; and (b) a film-forming component comprising:
  (i) at least one copolymerized monoethylenically unsaturated (meth)acrylic acid ester comprising an alkyl group having less that 4 carbons on average; and
  (ii) at least one copolymerized ethylenically unsaturated hydrophilic acidic monomer.

This adhesive is described in WO 00/78885.

Particularly preferred embodiments of the present invention comprise hot melt adhesives that are formulated to provide low trauma removal from skin. Most preferably, the adhesive composite of the present invention may be removed from skin without noticeable damage thereto. This embodiment finds particular benefit when the adhesive composite is used on elderly patients or those having extremely sensitive or fragile skin. Additionally, low trauma adhesives are easily removed from cloth drape materials without leaving adhesive residue on the drape, which provides particular benefit in laundering and reuse of surgical drapes. Residue evaluation is carried out by first applying an adhesive composite to a cloth drape, and applying pressure by rolling with six passes of a 4.5 pound (2.04 kg) roller, and leaving the adhesive composite in place on the cloth drape for 8 hours. The adhesive composite is then removed, and the cloth drape is visually inspected for residue. Preferably, no adhesive residue is visible on the cloth drape.

A particularly preferred low trauma adhesive composition is a fiber reinforced adhesive composition comprising a pressure sensitive adhesive matrix and a fibrous reinforcing material within the pressure sensitive adhesive matrix. This fiber reinforced adhesive composition allows for an improved cohesive strength over the pressure sensitive adhesive alone, yet the tack of the pressure sensitive adhesive remains substantially unreduced. The particular format of this adhesive composition provides for stretch release of the adhesive composite. Thus, the adhesive composite can be readily removed by pulling and elongating the adhesive composite, preferably at a rate of 30 cm/minute and at an angle of no greater than 45°. Stretch release embodiments preferably include a highly extensible and easily extensible backing. This removal process results in the detachment of the adhesive composite from the substrate without significant damage to the substrate surface and without leaving a significant residue.

The fiber of the reinforcing material is preferably formed from a polymer in situ. Thus, the hot melt adhesive composite prior to coating on the substrate is provided with a semicrystalline polymer distributed therein. The reinforcing material preferably is immiscible in the adhesive composition, so that it may be substantially uniformly dispersed in the pressure sensitive adhesive. Preferably, the reinforcing material is in the form of substantially spherical particles having an average diameter less than about 20 micrometers. Optionally, the reinforcing material may be provided as a component of the adhesive composition, or may be added as a separate component together with the other components of the hot melt coatable adhesive at the time of mixing in the hot melt mixer.

During coating of the hot melt coatable adhesive, the mixture is subjected to an elongating shear force. The resulting coated adhesive contains the reinforcing material, which is present as substantially continuous fibers in the adhesive.

Preferred adhesive compositions to prepare stretch release adhesives are prepared in accordance with disclosure of U.S. patent Publication No. 2002/0164446-A1 (Zhou, et. al.).

Hot melt coatable adhesive compositions are preferably provided in melt processable packaging for easy handling of the composition in the processing steps. Additionally, the hot melt coatable adhesive, when not immediately coated to form an adhesive composite, is also preferably packaged in melt processable packaging for easy handling in subsequent hot melt coating operations.

The melt processable packaging material is made of a material that when combined with the adhesive does not substantially adversely affect the desired adhesive characteristics. A hot melt coated adhesive produced from a mixture of the adhesive and the packaging material may have improved adhesive properties compared to hot melt coated adhesive produced from adhesive alone. The packaging material preferably melts at or below the processing temperature of the adhesive (i.e., the temperature at which the adhesive flows). The packaging material preferably has a melting point of 200° C. or less, preferably 170° C. or less. In a preferred embodiment, the melting point ranges from 90° C. to 150° C. The packaging material may be a flexible thermoplastic polymeric film. The packaging material is preferably selected from ethylene-vinyl acetate, ethylene-acrylic acid, polypropylene, polyethylene, polybutadiene, or ionomeric films. In a preferred embodiment the packaging material is an ethylene-acrylic acid or ethylene-vinyl acetate film.

The amount of packaging material depends upon the type of material and the desired end properties. The amount of packaging material typically ranges from about 0.5 percent to about 20 percent of the total weight of the pre-adhesive composition and the packaging material. Preferably, the packaging material is between 2 percent and 15 percent by weight, and more preferably between 3 percent and 5 percent. Such packaging materials may contain plasticizers, stabilizers, dyes, perfumes, fillers, slip agents, antiblock agents, flame retardants, anti-static agents, microwave susceptors, thermally conductive particles, electrically conductive particles, and/or other materials to increase the flexibility, handleability, visibility, or other useful property of the film, as long as they do not adversely affect the desired properties of the adhesive.

In certain embodiments, it may be desirable to carry out a polymerization step of ingredients of the pre-adhesive composition within the packaging prior to utilization in a hot melt mixing or coating process. In these embodiments, the packaging material should be appropriate for the polymerization method used. For example, with photopolymerization, it is necessary to use a film material that is sufficiently transparent to ultraviolet radiation at the wavelengths necessary to effect polymerization.

Thermal polymerization of the pre-adhesive composition can be effected by immersing the packaged composition in a heat exchange medium at temperatures from about 40° C. to about 100° C. for a time sufficient to polymerize the composition. The heat exchange medium may be a forced or impinged gas or a liquid such as water, perfluorinated liquids, glycerine, or propylene glycol. The heat necessary for thermal polymerization may also be provided by a metal platen, heated metal rolls, or microwave energy.

The polymerized adhesives may be used to make a coatable thermoplastic or thermosettable hot melt adhesive by introducing the adhesive and its packaging material into a vessel in which the adhesive and its packaging material are melted. By "homogeneous mixing" is meant that the composition has attained a uniform concentration of iodine and iodide throughout the adhesive matrix. Characteristically, the preferred coated adhesives of the present invention have a uniform color when coated at a uniform thickness on a backing or liner, so that no color variation is visibly discernible on unmagnified visual inspection.

The hot melt mixer is any appropriate device that will provide consistent mixing of the $I_2/I^-$ composition, the iodine/iodide complexing agent, and the adhesive composition at the desired temperature range. When the iodine/iodide-containing hot melt coatable adhesive is prepared for intermediate storage, with coating on a substrate to be performed later, the hot melt mixer is preferably a bulk tank melter or melt-on-demand equipment, either of which is fitted with a mixing apparatus. Melt blending devices include those that provide dispersive mixing, distributive mixing, or a combination of dispersive and distributive mixing. Both batch and continuous methods of melt blending can be used. Examples of batch methods include those using a BRABENDER (e.g. a BRABENDER PREP CENTER, commercially available from C.W. Brabender Instruments, Inc.; South Hackensack, N.J.) or BANBURY internal mixing and roll milling equipment (e.g. equipment available from Farrel Co.; Ansonia, Conn.). After batch mixing, the mixture created may be immediately quenched and stored below melting temperature of the mixture for later processing. In the event that the iodine/iodide-containing hot melt coatable adhesive is to be immediately coated onto a substrate, the hot melt mixer is preferably a heated extruder (preferably using a continuous extrusion method) or a hand-held hot melt adhesive gun. Examples of continuous methods of melt blending include single screw extruding, twin screw extruding, disk extruding, reciprocating single screw extruding, and pin barrel single screw extruding. The continuous methods can include utilizing both distributive elements, such as cavity transfer mixers (e.g. CTM, commercially available from RAPRA Technology, Ltd.; Shrewsbury, England) and pin mixing elements, static mixing elements or dispersive mixing elements (commercially available from e.g., MADDOCK mixing elements or SAXTON mixing elements as described in "Mixing in Single-Screw Extruders," *Mixing in Polymer Processing*, edited by Chris Rauwendaal (Marcel Dekker elements or SAXTON mixing elements as described in "Mixing in Single-Screw Extruders," *Mixing in Polymer Processing*, edited by Chris Rauwendaal (Marcel Dekker Inc.: New York (1991), pp. 129, 176-177, and 185-186).

When the iodine/iodide-containing hot melt coatable adhesive is prepared for intermediate storage, with coating on a substrate to be performed later, the adhesive is preferably packaged in a melt processable packaging material as described above.

The hot melt coatable adhesive may be used to form an adhesive composite sheet by coating the adhesive on a sheet material or another suitable substrate. The sheet material is preferably selected from a tape backing or a release liner. If a crosslinking agent is added, the coated adhesive can then be exposed to sufficient UV radiation or ionizing radiation to effect the crosslinking. Crosslinking is preferably initiated after coating.

Preferably, the adhesive composite is formed by continuous forming methods; including hot melt coating, drawing or extruding; the adhesive composition from the elongating shear force device (e.g. a draw die, a film die, or a rotary rod die) and subsequently contacting the drawn adhesive composition to a moving web (e.g. plastic) or other suitable substrate. A related continuous forming method involves extruding the adhesive composition and a co-extruded backing material from a film die and cooling the layered product to form an adhesive tape. Other continuous forming methods involve directly contacting the adhesive composition to a rapidly moving web or other suitable preformed substrate. Using this method, the adhesive composition is applied to the moving preformed web using a die having flexible die lips, such as a rotary rod die. The coated hot melt adhesive may optionally be cooled after coating, For example, the temperature may be lowered by quenching the adhesive composition using either direct methods (e.g., chill rolls or water baths) or indirect methods (e.g., air or gas impingement).

In one embodiment of the invention, a tape, wound dressing, surgical incise drape and the like is formed in which the substrate is an appropriate backing. Typical tape backings include cellulosic materials such as paper, crepe paper, and cloth (including both woven and non-woven cloths); films such as biaxially oriented polyester, polyvinyl chloride, polyurethane, elastomeric polyesters, biaxially and monoaxially oriented polypropylene, and nylon; foam materials such as polyethylene foams and acrylic foams; and metal foils such as aluminum foil. Preferably, incise drapes are formed from a transparent or translucent polymeric material. The material preferably allows for moisture evaporation through the film during prolonged surgeries. Particularly suitable materials for incise drapes include polyolefins, such as low density polyethylene and particularly metallocene polyethylenes such as Engage™ polyethylenes commercially available from Dow Chemical, polyurethanes such as polyester or polyether polyurethanes (e.g., "Estane™ thermoplastic polyurethane," commercially available from B. F. Goodrich, Cleveland Ohio), polyesters such as polyether polyester (e.g., "Hytrel™ polyester elastomer," commercially available from Du Pont Co., Wilmington, Del.), and polyamides such as polyether polyamides (e.g., "Pebax™ Resins" commercially available from ELF Atochem, North America, Inc., Philadelphia, Pa.).

For products wound onto themselves without a liner such as tape products, the backings are usually treated on the back side with a release coating such as silicone, and may be treated prior to hot melt coating to enhance the adhesion of the adhesive to the backing. Treatments useful for enhancing the adhesion of the adhesive to the backing include chemical priming and corona treatment.

In another embodiment of the invention, a transfer tape is formed wherein the substrate is a release liner. The release liner can be coated on one or both sides with a release coating, and the transfer tape is removed from the substrate when used by the end user. The release liner may be made of a variety of materials such as paper, plastic coated paper, plastic film, woven, non-woven, or knit textiles, as well as film textile laminates. The liner may be hydrophilic to allow fluid absorbency or may be hydrophobic without absorbency. Preferred release liner materials, particularly in the incise drape embodiment of the present invention, include clear polymeric liners that allow the clinician to see through to the patient and thus accurately place the film during application of the film to a patient. Preferred clear polymeric liners include polyolefins such as polyethylene and polypropylene, or polyester liners, as well as laminates such as polyolefin coated polyester. For products intended for gamma sterilization, use of a paper, polyethylene, polyester, or polyethylene coated polyester liner is preferred.

In specific embodiments, the adhesive compositions of the present invention are used in tapes that include gauze pads, for example, and are used as first aid dressings (i.e., wound or surgical dressings). They can also be used in a wide variety of other medical articles, such as medical tapes, athletic tapes, surgical drapes, or tapes or tabs used in adhering medical devices such as sensors, electrodes (as disclosed in U.S. Pat. No. 5,215,087 and U.S. Pat. No. 6,171,985, for example), ostomy appliances, or the like.

In a particularly preferred embodiment, the adhesive composite of the present invention is a surgical incise drape. Surgical incise drapes containing an antimicrobial in the adhesive are generally described in U.S. Pat. Nos. 4,310,509; 4,323,557; and 5,979,450.

The present invention will be further illustrated by the following nonlimiting examples.

EXAMPLES

| Acronym | Trade Designation and/or Description | Source/Address |
|---------|--------------------------------------|----------------|
| | GLOSSARY | |
| PVPI | povidone iodine | BASF Corp. Mt. Olive, NJ |
| 2EHA | 2-ethylhexyl acrylate | BASF Corp. Mt. Olive, NJ |
| AA | acrylic acid | BASF Corp. Mt. Olive, NJ |
| PPEG | PYCAL 94/phenoxy polyethylene glycol | ICI Chemical, Inc. Wilmington, DE |
| EPPG | UCON 50H400, ethylene/propylene glycol | Union Carbide-Dow Corp. Danbury, CT |
| PG | propylene glycol | Sigma-Aldrich Chemical Co. St. Louis, MO |
| 2PE | 2-phenoxy ethanol | Sigma-Aldrich Chemical Co. St. Louis, MO |
| MPD | 2-methyl 1,3-propanediol | Lyondell Chemical Worldwide Inc., Houston, TX |

-continued

GLOSSARY

| Acronym | Trade Designation and/or Description | Source/Address |
|---|---|---|
| MMB | 3-methoxy 3-methyl, 1-butanol | CBC America Corp. New York, NY |
| MPEG 550 | CARBOWAX MPEG 550/A methoxypolyethylene glycol having a molecular weight of approximately 550 | Union Carbide-Dow Corp. Danbury, CT |
| Irg 651 | IRGACURE 651/A 2,2-dimethoxy-2-phenyl acetophenone photoinitiator | Ciba Specialty Chemical Corp. Tarrytown, NY |
| Irg 1076 | IRGANOX 1076/An octadecyl 8 (e, 5-tert-gutyl-4-hydroxyphenol) propionate antioxidant | Ciba Specialty Chemical Corp. Tarrytown, NY |
| IOTG | isooctyl thioglycolate | Hampshire (sub of Dow Chemical) Lexington, MA |
| TegMerR 804 | TegMerR 804/tetraethyleneglycol di-2ethylhexanoate | CP Hall Company Chicago, IL |
| TegMerR 809 | TegMerR 809/PEG 400 di-2ethylhexanoate | CP Hall Company Chicago, IL |
| PEG 400 | CARBOWAX 400, polyethylene glycol having a MW of about 400 | Union Carbide-Dow Corp. Danbury, CT |
| CPH-30N | CPH-30N/PEG 400 monolaurate | CP Hall Company Chicago, IL |
| PHE3040 | Exact 3040/poly(ethylene-co-hexene) polymer resin | ExxonMobil Chemical Corp. Houston, TX |
| IOA | isooctyl acrylate | 3M Company St. Paul, MN |
| NVP | n-vinyl pyrollidone | BASF Corp. Mt. Olive, NJ |
| POE 10 | Attane 4202/poly (octene-co-ethylene) resin | Dow Chemical Co., Midland, MI |
| NVC | n-vinyl caprolactam | BASF Corp. Mt. Olive, NJ |
| $I_2$ | iodine | Deepwater Chemicals Woodward, OK |
| NaI | sodium iodide | Deepwater Chemicals Woodward, OK |

Examples 1-4

Adhesive compositions containing relatively high levels of AA with different levels of glycol and povidone iodine (PVPI) were prepared. First, adhesive monomers and glycol plasticizer were packaged in ethylene vinyl acetate (EVA) pouches as described in U.S. Pat. No. 5,804,610 using a composition of 33/33/33 AA/2EHA/PPEG. The contents of the pouches were polymerized by exposing them to UV-A radiation for 10 minutes, submerged in water at a temperature of 16° C with the UV intensity measured at a 0.0254 cm (1 inch) at an immersion depth of 3.5 mW per $cm^2$.

Components, PVPI, PPEG and MPEG 55, were added sequentially and mixed in the amounts indicated in Table 1 using a Prep Center melt mixer (commercially available from C. W. Brabender, Hackensack N.J.) using the 30 milliliter bowl with two sigma mixing blades at a temperature of 110° C. After each addition, the adhesive composition was mixed for about 10 minutes prior to proceeding to the next step. The compounded adhesives were removed from the Brabender mixer and coated on a 0.0508 mm (2 mil) thick release surface of siliconized PET film (commercially available from C.P. Films, Inc., Martinsville, Va.) at 154° C. using a laboratory scale melt mixing and coating device. The device melt mixes by forcing a heated and melted polymer over a three-element static mix section reciprocally, a finite number of times (60 cycles, where one cycle is two passes over the static mix section) to achieve adequate mixing. A valve redirects flow through a small draw die, into a coat hanger shaped cavity with a 5.08 cm (2-inch) wide by 0.0127 cm (0.005 inch) orifice which is heated to the same temperature as the melt chambers. The adhesive coating thickness was 0.0508-0.0762 mm (2-3 mils).

After the adhesive was coated on to the liner, a person's thumb was pressed onto the surface to evaluate the surface with respect to the relative tackiness and described as tacky or not tacky and the relative hardness described as stiff or soft. The appearance of the adhesive was observed for uniformity and described as uniform, less uniform or not uniform. Uniform means the thickness of coated adhesive was even, with no visible particles or chunks present in the coated adhesive. Less uniform means the thickness of coated adhesive was even, but there were some small particles present in the adhesive. Not uniform means the thickness was not even and there were many particles or chunks present in the adhesive. The color was also noted. Relative transparency was also observed and described as opaque, transparent, and more transparent. The results of the coated adhesive evaluation are shown in Table 1.

TABLE 1

Composition of the compounded adhesive and results of the coated adhesive evaluation.

| Example Number | AA/2EHA/ PPEG Adhesive Amount (g) | PVPI Amount (g) | PPEG Amount (g) | MPEG 550 Amount (g) | Surface Tack and Hardness (Tacky or not tacky) (Stiff or soft) | Appearance (Uniform) (Color) |
|---|---|---|---|---|---|---|
| 1 | 30.00 | 1.54 | 0.00 | 0.00 | Not tacky, Stiff | Uniform light yellow color |
| 2 | 30.00 | 1.61 | 1.50 | 0.00 | Not tacky, Stiff | Uniform light yellow color |
| 3 | 30.00 | 1.56 | 0.00 | 1.40 | Tacky, Soft | More transparent Uniform light yellow color |
| 4 | 30.00 | 3.23 | 0.00 | 2.83 | Not tacky, Stiff | Uniform light yellow color |

Examples 5-34

Adhesive compositions containing relatively high levels of AA with different levels of a non-aqueous iodine ($I_2$) solution and an aqueous sodium iodide (NaI) solution were prepared. First the six adhesive polymers (A-F) were created as described in Examples 1-4 having the compositions shown in Table 2.

TABLE 2

Composition of Adhesive Polymer A-F

| Adhesive Polymer | 2-EHA Amount (g) | AA Amount (g) | NVP Amount (g) | 10% IOTG Amount (g) | 10% Irg 651 Amount (g) | 10% Irg 1076 Amount (g) | PPEG Amount (g) | EPPG Amount (g) |
|---|---|---|---|---|---|---|---|---|
| A | 38.9 | 50.0 | 5.0 | 0.6 | 1.5 | 4.0 | 70.0 | 0.0 |
| B | 43.9 | 45.0 | 5.0 | 0.6 | 1.5 | 4.0 | 60.0 | 0.0 |
| C | 48.9 | 40.0 | 5.0 | 0.6 | 1.5 | 4.0 | 50.0 | 0.0 |
| D | 38.9 | 50.0 | 5.0 | 0.6 | 1.5 | 4.0 | 0.0 | 70.0 |
| E | 43.9 | 45.0 | 5.0 | 0.6 | 1.5 | 4.0 | 0.0 | 60.0 |
| F | 48.9 | 40.0 | 5.0 | 0.6 | 1.5 | 4.0 | 0.0 | 50.0 |

Elemental iodine ($I_2$) was dissolved in four different liquids: TegMerR 804, TegMerR 809, CPH-30N and PPEG to obtain an 18 percent by weight solutions. The solutions were placed in glass vials, which were rolled on a roller overnight so that no crystals were left and the final solutions were dark red.

Sodium iodide (NaI) powder was dissolved completely in deionized water to form a clear 50 percent by weight solution.

Adhesive polymers A-F in Table 2 were each mixed with 1.2 grams of 50 percent NaI aqueous solution and 2.8 grams of 18 percent $I_2$ non-aqueous solution using the Brabender mixer at 110° C. for about 15 minutes. The compounded adhesives were then coated using the laboratory scale melt mixing and coating device as described Examples 1-4. The backing material was the same 0.0508 mm (2-mil) thick PET film described in Examples 1-4. The coating thickness was about 0.0508 mm (2 mils). Surprisingly, during extrusion little or no iodine was observed to volatilize into the atmosphere during the melt mixing.

The appearance of the coated adhesives was recorded as uniform, less uniform, and not uniform. Uniform means the thickness of coated adhesive was even, with no particles or chunks visibly present in the coated adhesive. Less uniform means the thickness of coated adhesive was even, but there were some small particles present in the adhesive. Not uniform means the thickness was not even and there were many particles or chunks present in the adhesive. The compositions and results are shown in Table 3.

TABLE 3

Compositions and Appearance of Examples 5-34.

| Ex. No. | $I_2$ in CPH-30 Amount (g) | $I_2$ in Tegmer 809 Amount (g) | $I_2$ in Tegmer 804 Amount (g) | $I_2$ in PPEG Amount (g) | NaI in Water Amount (g) | Adhesive Polymers from Table 2 Amount (g) | | | | | | Appearance (Uniform, less uniform, not uniform) |
|---|---|---|---|---|---|---|---|---|---|---|---|---|
| | | | | | | A | B | C | D | E | F | |
| 5 | 2.8 | 0.0 | 0.0 | 0.0 | 1.2 | 25.0 | 0.0 | 0.0 | 0.0 | 0.0 | 0.0 | Uniform |
| 6 | 0.0 | 2.8 | 0.0 | 0.0 | 1.2 | 25.0 | 0.0 | 0.0 | 0.0 | 0.0 | 0.0 | Uniform |
| 7 | 0.0 | 0.0 | 2.8 | 0.0 | 1.2 | 25.0 | 0.0 | 0.0 | 0.0 | 0.0 | 0.0 | Uniform |
| 8 | 0.0 | 0.0 | 0.0 | 2.8 | 1.2 | 25.0 | 0.0 | 0.0 | 0.0 | 0.0 | 0.0 | Uniform |
| 9 | 0.0 | 0.0 | 0.0 | 0.0 | 0.0 | 25.0 | 0.0 | 0.0 | 0.0 | 0.0 | 0.0 | NA[1] |
| 10 | 2.8 | 0.0 | 0.0 | 0.0 | 1.2 | 0.0 | 25.0 | 0.0 | 0.0 | 0.0 | 0.0 | Uniform |
| 11 | 0.0 | 2.8 | 0.0 | 0.0 | 1.2 | 0.0 | 25.0 | 0.0 | 0.0 | 0.0 | 0.0 | Less uniform |
| 12 | 0.0 | 0.0 | 2.8 | 0.0 | 1.2 | 0.0 | 25.0 | 0.0 | 0.0 | 0.0 | 0.0 | Less uniform |
| 13 | 0.0 | 0.0 | 0.0 | 2.8 | 1.2 | 0.0 | 25.0 | 0.0 | 0.0 | 0.0 | 0.0 | Not Uniform |
| 14 | 0.0 | 0.0 | 0.0 | 0.0 | 0.0 | 0.0 | 25.0 | 0.0 | 0.0 | 0.0 | 0.0 | NA |
| 15 | 2.8 | 0.0 | 0.0 | 0.0 | 1.2 | 0.0 | 0.0 | 25.0 | 0.0 | 0.0 | 0.0 | Not Uniform |
| 16 | 0.0 | 2.8 | 0.0 | 0.0 | 1.2 | 0.0 | 0.0 | 25.0 | 0.0 | 0.0 | 0.0 | Less uniform |
| 17 | 0.0 | 0.0 | 2.8 | 0.0 | 1.2 | 0.0 | 0.0 | 25.0 | 0.0 | 0.0 | 0.0 | Not uniform |
| 18 | 0.0 | 0.0 | 0.0 | 2.8 | 1.2 | 0.0 | 0.0 | 25.0 | 0.0 | 0.0 | 0.0 | Not uniform |
| 19 | 0.0 | 0.0 | 0.0 | 0.0 | 0.0 | 0.0 | 0.0 | 25.0 | 0.0 | 0.0 | 0.0 | NA |
| 20 | 2.8 | 0.0 | 0.0 | 0.0 | 1.2 | 0.0 | 0.0 | 0.0 | 25.0 | 0.0 | 0.0 | Not uniform |
| 21 | 0.0 | 2.8 | 0.0 | 0.0 | 1.2 | 0.0 | 0.0 | 0.0 | 25.0 | 0.0 | 0.0 | Not uniform |

TABLE 3-continued

Compositions and Appearance of Examples 5-34.

| Ex. No. | I₂ in CPH-30 Amount (g) | I₂ in Tegmer 809 Amount (g) | I₂ in Tegmer 804 Amount (g) | I₂ in PPEG Amount (g) | NaI in Water Amount (g) | Adhesive Polymers from Table 2 Amount (g) | | | | | | Appearance (Uniform, less uniform, not uniform) |
|---|---|---|---|---|---|---|---|---|---|---|---|---|
| | | | | | | A | B | C | D | E | F | |
| 22 | 0.0 | 0.0 | 2.8 | 0.0 | 1.2 | 0.0 | 0.0 | 0.0 | 25.0 | 0.0 | 0.0 | Less uniform |
| 23 | 0.0 | 0.0 | 0.0 | 2.8 | 1.2 | 0.0 | 0.0 | 0.0 | 25.0 | 0.0 | 0.0 | Less uniform |
| 24 | 0.0 | 0.0 | 0.0 | 0.0 | 0.0 | 0.0 | 0.0 | 0.0 | 25.0 | 0.0 | 0.0 | Less uniform |
| 25 | 2.8 | 0.0 | 0.0 | 0.0 | 1.2 | 0.0 | 0.0 | 0.0 | 0.0 | 25.0 | 0.0 | NA |
| 26 | 0.0 | 2.8 | 0.0 | 0.0 | 1.2 | 0.0 | 0.0 | 0.0 | 0.0 | 25.0 | 0.0 | Uniform |
| 27 | 0.0 | 0.0 | 2.8 | 0.0 | 1.2 | 0.0 | 0.0 | 0.0 | 0.0 | 25.0 | 0.0 | Uniform |
| 28 | 0.0 | 0.0 | 0.0 | 2.8 | 1.2 | 0.0 | 0.0 | 0.0 | 0.0 | 25.0 | 0.0 | Not uniform |
| 29 | 0.0 | 0.0 | 0.0 | 0.0 | 0.0 | 0.0 | 0.0 | 0.0 | 0.0 | 25.0 | 0.0 | NA |
| 30 | 2.8 | 0.0 | 0.0 | 0.0 | 1.2 | 0.0 | 0.0 | 0.0 | 0.0 | 0.0 | 25.0 | Uniform |
| 31 | 0.0 | 2.8 | 0.0 | 0.0 | 1.2 | 0.0 | 0.0 | 0.0 | 0.0 | 0.0 | 25.0 | Less uniform |
| 32 | 0.0 | 0.0 | 2.8 | 0.0 | 1.2 | 0.0 | 0.0 | 0.0 | 0.0 | 0.0 | 25.0 | Not uniform |
| 33 | 0.0 | 0.0 | 0.0 | 2.8 | 1.2 | 0.0 | 0.0 | 0.0 | 0.0 | 0.0 | 25.0 | Uniform |
| 34 | 0.0 | 0.0 | 0.0 | 0.0 | 0.0 | 0.0 | 0.0 | 0.0 | 0.0 | 0.0 | 25.0 | NA |

[1]NA means not applicable

[1]NA Means not Applicable

In-vitro antimicrobial efficacy tests were performed on samples taken from Examples 5-34 using direct inoculation assay (Qualitative testing method). Additionally, a peel adhesion test was performed.

Direct Inoculation Assay:

Samples were prepared by using Scotch® Permanent Double Stick Tape No. 137 (3M Company, St. Paul, Minn.) to attach the 3.9 cm² samples, adhesive side up in the bottom of a labeled six-well tissue culture plate. The six-well plates containing the drape samples were gamma-sterilized using a dose of 25 kilograys.

Each sample was inoculated with 50 micro liters of a suspension of *Entercoccus faecalis*, ATCC 10741 (approx. 9.0× 10⁸ cfu/ml) by spotting droplets across the surface of the adhesive. Inoculated samples were incubated at 37° C. in a humidified incubator until the predetermined time point was reached. The time points were 10 minutes, 30 minutes, 60 minutes and 120 minutes. When possible, the samples were tested in triplicate per time point.

Once the time point was reached, the samples were removed from the incubator and 2 ml of Brain Heart Infusion broth with 0.1% sodium thiosulfate was added to each sample well. After the broth was added to each well, the plate was placed back in the incubator overnight. The following day each plate was evaluated for turbidity to determine an endpoint of growth or no growth. Due to sample interference, presence of growth was confirmed by streaking onto Tryticase Soy Agar (TSA). The results were reported as (+) for growth and (−) for no growth.

Comparison Example 1

A solvent-coated adhesive composition was prepared as described in U.S. Pat. No. 4,323,557 (Rosso et al.) comprising 2% iodine and 2.4 % sodium iodide by weight. It was solvent coated on a silicone release liner and dried to form a homogeneous, iodine-colored adhesive film with a coating thickness of 0.037 mm (1.5 mil.). This comparison example (C1) was used as a standard to compare the results of antimicrobial efficacy for Examples 5-34 in Table 4, Examples 35-42 in Table 6, Examples 43-47 in Table 9, Examples 48-59 in Table 12, Examples 60-62 in Table 14, Examples 63-64 in Table 16.

180 Degree Peel Adhesion Test:

Compounded Adhesives were coated onto the release surface of siliconized PET film as described in Examples 1-4 at a thickness of about 0.0508 mm (2 mil). The air surface of the adhesive was covered with 53# Poly coated Kraft paper liner. Samples were cut to 1.27 cm (½" wide) and approximately 25.4 cm (10 inches) long. Peel test samples were applied to a glass surface by making 6 passes with a 2.04 kg (4.5 lb) roller and waiting one minute prior to peeling. The adhesive coated film was peeled off the glass substrate at 30.5 cm per minute at a 180° angle for 5 seconds on an Imass Peel Tester Model SP 2000 commercially available from IMASS INC., Accord Mass.). Peel values were measured in ounces/½ inch and reported in Newton/meter (N/m).

TABLE 4

Results of the Antimicrobial Efficacy and the Peel Adhesion Test of Examples 5-34 and Comparison Example 1.

| Sample from Example Number | After 10 min | | | After 30 min | | | After 60 min | | | After 120 min | | | Peel Adhesion |
|---|---|---|---|---|---|---|---|---|---|---|---|---|---|
| | Rep 1 | Rep 2 | Rep 3 | Rep 1 | Rep 2 | Rep 3 | Rep 1 | Rep 2 | Rep 3 | Rep 1 | Rep 2 | Rep 3 | (N/m) |
| C1 | + | + | + | + | + | + | + | + | + | − | − | − | NA[1] |
| 5 | − | − | − | − | − | − | − | − | − | − | − | − | 482 |
| 6 | + | + | + | − | − | − | − | − | − | − | − | − | 563 |
| 7 | − | − | − | − | − | − | − | − | − | − | − | − | 558 |
| 8 | − | − | − | − | − | − | − | − | − | − | − | − | 547 |
| 9 | + | + | + | + | + | + | + | + | + | + | + | + | 201 |
| 10 | − | − | − | − | − | − | − | − | − | − | − | − | 355 |
| 11 | − | − | − | − | − | − | − | − | − | − | − | − | 407 |
| 12 | − | − | − | − | − | − | − | − | − | − | − | − | 404 |
| 13 | − | − | − | − | − | − | − | − | − | − | − | − | 368 |
| 14 | + | + | + | + | + | + | + | + | + | + | + | + | 265 |
| 15 | − | − | − | + | − | − | − | − | − | − | − | − | 475 |
| 16 | − | − | − | − | − | − | − | − | − | − | − | − | 447 |
| 17 | − | − | − | − | − | − | − | − | − | − | − | − | 482 |
| 18 | − | − | − | + | − | − | − | − | − | − | − | − | 444 |
| 19 | + | + | + | + | + | + | + | + | + | + | + | + | 403 |
| 20 | − | − | − | − | − | − | − | − | − | − | − | − | 420 |
| 21 | − | − | − | − | − | − | − | − | − | − | − | − | 532 |
| 22 | − | − | − | − | − | − | − | − | − | − | − | − | 493 |
| 23 | − | − | − | − | − | − | − | − | − | − | − | − | 543 |
| 24 | + | + | + | + | + | + | + | + | + | + | + | + | 523 |
| 25 | − | − | − | − | − | − | − | − | − | − | − | − | 468 |
| 26 | − | − | − | − | − | − | − | − | − | − | − | − | 644 |
| 27 | − | − | − | − | − | − | − | − | − | − | − | − | 578 |
| 28 | − | − | − | − | − | − | − | − | − | + | − | − | 523 |
| 29 | + | + | + | + | + | + | + | + | + | + | + | + | 468 |
| 30 | + | + | + | − | − | − | − | − | − | − | − | − | 517 |
| 31 | − | − | + | − | − | − | − | − | − | − | − | − | 506 |
| 32 | − | − | − | − | − | − | − | − | − | − | − | − | 598 |
| 33 | − | − | − | − | − | − | − | − | − | − | − | − | NA |
| 34 | + | + | + | + | + | + | + | + | + | + | + | + | 545 |

[1]means Not Applicable

The peel adhesion of all samples was acceptable and ranged from 201-644 N/m. Iodine containing adhesives appeared to perform better and had peel adhesion values of 355 to 644 N/M. The antimicrobial efficacy of samples 5, 7, 8, 10-13, 15-18, 20-23, 25-28, and 31-33 was exceptionally good. All microbes were killed in under 10 min. Examples 9, 14, 19, 24, 29, and 34 were negative controls (no iodine) and; therefore, they have no antimicrobial activity. This indicates that the antimicrobial activity was due to the iodine and not the adhesives.

Example 35-42

Adhesive compositions containing different levels of IOA and NVP were prepared. First two adhesive polymers (G-H) were created as described in Examples 1-4 having the compositions shown in Table 5.

TABLE 5

Composition of Adhesive Polymers G and H

| Adhesive Polymers | IOA Amount (g) | NVP Amount (g) | 10% IOTG Amount (g) | 10% Irg 651 Amount (g) | 10% Irg 1076 Amount (g) |
|---|---|---|---|---|---|
| G | 90.0 | 10.0 | 0.6 | 1.5 | 4.0 |
| H | 95.0 | 5.0 | 0.6 | 1.5 | 4.0 |

Adequate amounts of each of these adhesive polymers G and H were mixed first with 2.5 weight percent NaI aqueous solution and then with 2 weight percent $I_2$ powder and PHE3040 polymer resin in the Brabender mixer described in Examples 1-4 at 150° C. for about 10 minutes. The ratio of adhesive to PHE3040 was varied as shown in Table 6. The sodium iodide was mixed with the adhesive first for 5 or 6 minutes and then iodine was added. This was mixed briefly for another 4 or 5 minutes to avoid prolonged exposure to elevated temperature. Iodine evaporation is greatly reduced by using the complexing agents described herein. In addition, the compounding temperature and coating temperature was controlled between 140° C. and 160° C. Most of the examples were compounded and coated at 150° C. Care was taken to not go above 180° C., since iodine has a boiling point of 184° C.

The mixed adhesives were then coated using a Haake single screw extruder at 149° C. to 160° C. The adhesive was extruded onto silicone release liner (commercially avaliable as POLYSILK™ silicone release papers from James River Co., H. P. Smith Division, Bedford Park, Ill.), at a temperature of 150° C. to a thickness of approximately 0.002 and 0.005 inches (51 and 130 microns) as indicated in Table 6. Surprisingly, during extrusion little or no iodine loss was observed.

The final coated adhesives were tested according to the antimicrobial efficacy test described in Examples 5-34. The results of the direct inoculation assay are shown in Table 6.

TABLE 6

Compositions, Coating Thickness, and Results of Microbial Efficacy Test for Examples 35-41 and Comparison Example 1

| Ex. No. | Adhesive Polymer (%) | NVP/PHE 3040 30/40 (%) | Coating thickness (mm) | After 10 min | | | After 30 min | | | After 60 min | | | After 120 min | | |
|---|---|---|---|---|---|---|---|---|---|---|---|---|---|---|---|
| | | | | Rep 1 | Rep 2 | Rep 3 | Rep 1 | Rep 2 | Rep 3 | Rep 1 | Rep 2 | Rep 3 | Rep 1 | Rep 2 | Rep 3 |
| C1 | 0 | 0 | 0.0254 | + | + | + | + | + | + | + | + | + | − | − | − |
| 35 | 90 G | 10 | 0.0508 | + | + | + | + | + | + | + | + | + | − | − | + |
| 36 | 90 G | 10 | 0.1270 | + | + | + | + | + | + | + | + | + | − | − | − |
| 37 | 80 G | 20 | 0.0508 | + | + | + | + | + | + | + | + | + | − | − | − |
| 38 | 80 G | 20 | 0.1270 | + | + | NT[1] | + | + | + | + | − | + | − | − | − |
| 39 | 90 H | 10 | 0.0508 | + | + | + | + | + | + | − | − | + | − | − | − |
| 40 | 90 H | 10 | 0.1270 | + | + | NT | + | − | − | − | − | − | − | − | − |
| 41 | 80 H | 20 | 0.0508 | + | + | + | + | + | + | − | − | − | − | − | − |
| 42 | 80 H | 20 | 0.1270 | + | + | + | + | + | + | − | − | − | − | − | − |

[1] Not Tested

Examples 35-42 all contained iodine and sodium iodide and displayed some antimicrobial activity. Note that every example had complete kill of the microorganisms at 120 minutes. Samples 40-42 showed complete kill after only 60 minutes.

Examples 43-47

Adhesive polymer I was created in EVA pouches as described in Examples 1-4 with the composition shown in Table 7.

TABLE 7

Composition of Adhesive Polymer I

| Adhesive Polymer | IOA Amount (g) | NVP Amount (g) | 10% IOTG Amount (g) | 10% Irg 651 Amount (g) | 10% Irg 1076 Amount (g) |
|---|---|---|---|---|---|
| I | 91.00 | 9.00 | 0.03 | 0.15 | 0.30 |

In a plastic vessel, a concentrate of sodium iodide/iodine was prepared by dissolving 25 weight percent of NaI and mixing in 20 weight percent of iodine in deionized water. The composition was stirred until a solution was formed with no crystals left. The solution became a dark purple color.

The adhesive polymer I (IOA/NVP=91/9) with varying amounts of NaI/I$_2$ in aqueous solution and POE 10 resin (Table 8) was compounded and extrusion coated using a twin-screw extruder (HAAKE twin screw 18 millimeter extruder, from HAAKE Inc, Paramous, N.J.). The compounding temperature and coating temperature was about at the melting point of POE 10 resin (126° C.) for Examples 43-45 and at the flow temperature of adhesive (130° C. to 170° C.) in Examples 46-47. Both temperatures were below the boiling point of iodine (184° C.) to reduce the potential loss of iodine. The adhesive was extruded through a slot die onto a 0.0381 mm (1.5 mil) PET silicone release liner film (commercially available for DCP-Lohja Inc., Willowbrook, Ill.).

TABLE 8

Composition of Coated Adhesives for Examples 43-47

| Example Number | 91/9 IOA/NVP (weight %) | $I_2$ (weight %) | NaI (weight %) | POE 10 (weight %) |
|---|---|---|---|---|
| 43 | 95.50 | 2.00 | 2.50 | 0.00 |
| 44 | 93.25 | 3.00 | 3.75 | 0.00 |
| 45 | 91.00 | 4.00 | 5.00 | 0.00 |
| 46 | 85.50 | 2.00 | 2.50 | 10.00 |
| 47 | 83.25 | 3.00 | 3.25 | 10.00 |

The final coated adhesives were tested for antimicrobial efficacy using the direct inoculation assay and for Peel Adhesion using the methods described for Examples 5-34 except that after the adhesives were extruded onto the release liner the adhesive films were laminated to a bare PET film backing (0.0381 mm (1.5 mil) thick PET film)). The results of these tests are shown in Table 9.

TABLE 9

Results of the Antimicrobial Efficacy and the Peel Adhesion Test of Examples 43-47 and Comparison Example 1.

| Example Number | After 10 min | | | After 30 min | | | After 60 min | | | After 120 min | | | Peel Adhesion N/m |
|---|---|---|---|---|---|---|---|---|---|---|---|---|---|
| | Rep 1 | Rep 2 | Rep 3 | Rep 1 | Rep 2 | Rep 3 | Rep 1 | Rep 2 | Rep 3 | Rep 1 | Rep 2 | Rep 3 | |
| C1 | + | + | + | + | + | + | + | + | + | − | − | − | NA |
| 43 | + | + | + | + | + | + | + | + | + | − | − | − | 486 |
| 44 | + | + | + | + | + | + | − | − | − | − | − | − | 589 |
| 45 | + | + | + | + | − | + | − | − | − | − | − | − | 488 |
| 46 | + | + | + | + | + | + | + | + | + | − | − | − | 843 |
| 47 | + | + | + | + | + | + | − | − | − | − | − | − | 773 |

Examples 43-47 contained iodine/sodium iodide and they all showed good antimicrobial activity and good peel adhesion. Thus, the presence of the POE 10 did not change antimicrobial efficacy. Surprisingly, during extrusion little or no iodine loss was observed.

Combustion Analysis for Iodine for Examples 43, 45, 27

Total iodine was determined by Oxygen Flask combustion (according to Schöniger) and titration with Silver Nitrate (Aldrich). Samples were weighed to plus or minus 0.01 milligram, wrapped in ashless filter paper and folded inside a platinum mesh suspended in a flask containing 500-mL iodine. About 10 ml of water having a resistance of at least 18MΩ and twenty drops of 5 percent sodium bisulfite (EM Science) were added to the flask. The flask was flushed generously with pure oxygen, sealed, and inverted for ignition of the paper and sample with a 125 Watt focused projection lamp. A blast shield held the stopper in the inverted flask during combustion. After half an hour, the absorbing solutions were quantitatively transferred to a titration beaker. Another ten drops of sodium bisulfite were added, and the solution was acidified using three drops of bromocresol green indicator (EM Science) and several drops of concentrated nitric acid (Aldrich). The sample was then titrated with 0.005N silver nitrate using a silver billet combination electrode and a Metrohm 751 T automatic titrator. The measured weight percent of iodine for each Example is shown in Table 10. Dividing the measured iodine by the theoretical weight percent iodine and multiplying by 100 calculated the percent iodine recovered.

TABLE 10

Combustion Analysis for Iodine in Examples 43, 45, 27, and Comparison Example 1.

| Example Number | $I_2$/NaI (Weight %) | Theoretical Iodine (Weight %) | Measured Iodine (Weight %) | Percent Iodine Recovered |
|---|---|---|---|---|
| C1 | 2/2.4 | 4.03 | 3.48 | 86.4 |
| 43 | 2/2.5 | 4.12 | 3.91 | 94.9 |
| 45 | 4/5 | 8.23 | 6.61 | 80.3 |
| 27 | 1.7/2.1 | 3.56 | 2.74 | 77.0 |

The amount of iodine lost during the hot melt process (Examples 27, 43, and 45) was approximately the same as the amount of iodine lost during the solvent coating process (C1).

Examples 48-59

Adhesive polymer I whose composition is described in Table 7 was hot melt compounded in a twin screw extruder with 2/2.5 weight percent of iodine/sodium iodide in an aqueous solution and varying levels of POE 10 resin as shown in Table 11. The POE 10 resin was incorporated to provide a stretch release property.

TABLE 11

Composition of Coated Adhesives for Examples 48-59

| Example Number | 91/9 IOA/NVP (weight %) | $I_2$ (weight %) | NaI (weight %) | POE 10 (weight %) |
|---|---|---|---|---|
| 48 | 95.5 | 2.0 | 2.5 | 0.0 |
| 49 | 95.5 | 2.0 | 2.5 | 0.0 |
| 50 | 85.5 | 2.0 | 2.5 | 10.0 |
| 51 | 85.5 | 2.0 | 2.5 | 10.0 |
| 52 | 80.5 | 2.0 | 2.5 | 15.0 |
| 53 | 80.5 | 2.0 | 2.5 | 15.0 |
| 54 | 75.5 | 2.0 | 2.5 | 20.0 |
| 55 | 75.5 | 2.0 | 2.5 | 20.0 |
| 56 | 70.5 | 2.0 | 2.5 | 25.0 |
| 57 | 70.5 | 2.0 | 2.5 | 25.0 |
| 58 | 65.5 | 2.0 | 2.5 | 30.0 |
| 59 | 65.5 | 2.0 | 2.5 | 30.0 |

The process of compounding and coating the adhesives was the same as described for Examples 43-47. The coating thickness is shown in Table 12. No loss of iodine was evident in the compounding and extruding processes, indicating that the IOA/NVP copolymer adhesive effectively complexed the iodine.

The adhesives were coated on silicone release paper liner (commercially available as POLYSILK™ silicone release papers from James River Co.) and then laminated to bare PET film. The final coated adhesives were tested for antimicrobial efficacy using the direct inoculation assay using the methods described for Examples 5-34. The results of these tests are shown in Table 12.

TABLE 12

Coating Thickness and Results of the Antimicrobial Efficacy Testing of Examples 48-59 and Comparison Example 1.

| Example Number | Coating Thickness (mm) | 10 min Rep 1 | 10 min Rep 2 | 10 min Rep 3 | 30 min Rep 1 | 30 min Rep2 | 30 min Rep 3 | 60 min Rep 1 | 60 min Rep 2 | 60 min Rep 3 | 120 min Rep 1 | 120 min Rep 2 | 120 min Rep 3 |
|---|---|---|---|---|---|---|---|---|---|---|---|---|---|
| C1 | 0.0254 | + | + | + | + | + | + | + | + | + | − | − | − |
| 48 | 0.0508 | + | + | + | + | + | + | + | − | − | − | − | − |
| 49 | 0.1270 | + | + | + | + | + | + | − | − | − | − | − | − |
| 50 | 0.0508 | + | + | + | + | + | + | − | − | + | − | − | − |
| 51 | 0.1270 | + | + | + | + | + | + | − | + | − | − | − | − |
| 52 | 0.0508 | + | + | + | + | + | + | + | − | + | − | − | − |
| 53 | 0.1270 | + | + | + | + | + | + | + | + | + | − | − | − |
| 54 | 0.0508 | + | + | + | + | + | + | + | + | + | − | − | − |
| 55 | 0.1270 | + | + | + | + | + | + | + | + | + | − | − | − |
| 56 | 0.0508 | + | + | + | + | + | + | − | + | − | − | − | − |
| 57 | 0.1270 | + | + | + | + | + | + | + | + | + | − | − | − |
| 58 | 0.0508 | + | + | + | + | + | + | − | − | + | − | − | − |
| 59 | 0.1270 | + | + | + | + | + | + | + | + | + | − | − | − |

Antimicrobial activity of the hot melt coated PSA compositions was comparable to the control. Therefor, the POE 10 in the final adhesives did not change the antimicrobial efficacy.

Examples 60-62

Adhesive polymers containing IOA and NVC were produced in an EVA pouch as described in Examples 1-4. Adhesive polymers J, K, and L compositions are shown in Table 13.

TABLE 13

Compositions of Adhesive Polymers J, K, and L.

| Example Number | Adhesive Polymer | IOA Amount (g) | NVC Amount (g) | 10% Irg 651 Amount (g) | 10% IOTG Amount (g) | 10% Irg 1076 Amount (g) |
|---|---|---|---|---|---|---|
| 60 | J | 87.0 | 7.0 | 1.5 | 0.5 | 4.0 |
| 61 | K | 84.0 | 10.0 | 1.5 | 0.5 | 4.0 |
| 62 | L | 81.0 | 13.0 | 1.5 | 0.5 | 4.0 |

Multiple loading levels of $I_2$ crystal and NaI aqueous solution were compounded into the adhesive. First, 25 grams of adhesive polymers J, K, and L were each mixed with 1.2 grams of a 50 percent NaI aqueous solution and 2.8 grams of $I_2$ crystal on the Brabender mixer at 110° C. for about 15 minutes. The mixed adhesives were then coated using the laboratory scale melt mixing and coating device described in Examples 1-4 at 154° C. The backing material was the same 0.0508 mm (2 mil) thick PET film described in Examples 1-4. The coating thickness was about 0.0508 mm (2 mils). No loss of iodine was evident in the mixing and coating processes.

The final coated adhesives were tested for anti-microbial activity using the method of Examples 35-64. The results are listed below in Table 14.

TABLE 14

Results of Microbial Efficacy Test for Examples 60-62 and Comparison Example 1.

| Example Number | After 10 min | | | After 30 min | | | After 60 min | | | After 120 min | | |
|---|---|---|---|---|---|---|---|---|---|---|---|---|
| | Rep 1 | Rep 2 | Rep 3 | Rep 1 | Rep 2 | Rep 3 | Rep 1 | Rep 2 | Rep 3 | Rep 1 | Rep 2 | Rep 3 |
| C1 | + | + | + | + | + | + | + | + | + | − | − | − |
| 60 | + | + | + | + | + | + | − | − | + | − | − | − |
| 61 | + | + | + | + | + | + | + | + | + | − | − | − |
| 62 | + | + | + | + | + | + | + | + | + | − | − | − |

Every example had good antimicrobial activity, indicating that although the IOA/NVC copolymer adhesive effectively complexed the iodine even at very high temperatures, the iodine was still available to be released from the adhesive to kill microorganisms.

Examples 63-71

Adhesive compositions containing relative high levels of AA with different levels of various glycols were created in EVA pouches as described in Examples 1-4 using the compositions shown in the Table 15.

TABLE 15

Compositions of Examples 63-71

| Ex. No. | 2EHA (weight %) | AA (weight %) | 10% IOTG (weight %) | 10% Irg651 (weight %) | 10% Irg1076 (weight %) | PPEG (weight %) | PG (weight %) | 2PE (weight %) | MPD (weight %) | MMB (weight %) |
|---|---|---|---|---|---|---|---|---|---|---|
| 63 | 25.9 | 29.4 | 0.3 | 0.9 | 2.3 | 41.2 | 0.0 | 0.0 | 0.0 | 0.0 |
| 64 | 29.4 | 33.3 | 0.3 | 1.0 | 2.7 | 0.0 | 33.3 | 0.0 | 0.0 | 0.0 |
| 65 | 27.5 | 31.3 | 0.3 | 0.9 | 2.5 | 0.0 | 37.5 | 0.0 | 0.0 | 0.0 |
| 66 | 29.4 | 33.3 | 0.3 | 1.0 | 2.7 | 0.0 | 0.0 | 33.3 | 0.0 | 0.0 |
| 67 | 27.5 | 31.3 | 0.3 | 0.9 | 2.5 | 0.0 | 0.0 | 37.5 | 0.0 | 0.0 |
| 68 | 29.4 | 33.3 | 0.3 | 1.0 | 2.7 | 0.0 | 0.0 | 0.0 | 33.3 | 0.0 |
| 69 | 27.5 | 31.3 | 0.3 | 0.9 | 2.5 | 0.0 | 0.0 | 0.0 | 37.5 | 0.0 |
| 70 | 29.4 | 33.3 | 0.3 | 1.0 | 2.7 | 0.0 | 0.0 | 0.0 | 0.0 | 33.3 |
| 71 | 27.5 | 31.3 | 0.3 | 0.9 | 2.5 | 0.0 | 0.0 | 0.0 | 0.0 | 37.5 |

The adhesive compositions of Examples 63-71 were compounded with 4% of PVPI and coated using the laboratory scale melt mixing and coating device described in Examples 1-4 onto the same 0.0508 mm (2 mil) thick PET film described in Examples 1-4. Only examples 63 and 64 coated out uniformly. The coating thickness was 0.0508 mm (2 mil). The remainder of adhesives gelled on extrusion.

Examples 63 and 64 were evaluated for antimicrobial efficacy using the Direct Inoculation Assay as described for Examples 5-34. The results are summarized in Table 16.

TABLE 16

Results of Antimicrobial Efficacy Test for Examples 63, 64 and Comparison Example 1.

| Example Number | After 10 min | | | After 30 min | | | After 60 min | | | After 120 min | | |
|---|---|---|---|---|---|---|---|---|---|---|---|---|
| | Rep 1 | Rep 2 | Rep 3 | Rep 1 | Rep 2 | Rep 3 | Rep 1 | Rep 2 | Rep 3 | Rep 1 | Rep 2 | Rep 3 |
| C1 | + | + | + | + | + | + | + | + | + | − | − | − |
| 63 | + | + | + | + | + | + | + | + | + | − | − | − |
| 64 | + | + | + | + | + | + | − | − | − | − | − | − |

The samples had at least equivalent antimicrobial efficacy compared to the control. Example 64 which was one of the uniformly coated adhesives showed total kill at 60 minutes, which may indicate enhanced activity from the presence of the glycol.

Example 72

For this example the adhesive was compounded with a complexing agent (polyvinyl pyrrolidone/vinyl acetate (PVP/VA) copolymer) and iodine/sodium iodide in solvent. Alternatively, these components could be added to a hot melt mixer by a solvent free process.

The base adhesive polymer was 1663.3 gm of an adhesive consisting of a 97/3 iso-octylacrylate/acrylamide composition prepared as described in U.S. Pat. No. Re. 24,906 at 36% solids in a 50/50 heptane/ethyl acetate solvent mixture. Ethanol ((anhydrous, EM Science, Gibbstown, N.J.) 415.8 gm) was added to the base polymer with stirring until a uniform solution was achieved.

In a separate vessel, 74.88 gm ethanol, 83.2 gm of PVP/VA E-535 (a 50/50 vinylpyrrolidone/vinyl acetate copolymer made by International Specialty Products, Wayne, N.J.), 8.32 gm iodine (Mallinckrodt Chemical St. Louis, Mo.), and 9.98 gm sodium iodide (Fisher Scientific, Fair Lawn, N.J.) were added and stirred until a solution was made. The iodine/iodide solution was then added to the adhesive and stirred until a consistent, uniformly colored solution was prepared. The adhesive/iodine solution was poured onto a silicone liner (Daubert Coated Products, Dixon Ill.) and placed in a forced air oven (Model POM-1506G Blue M Company, Blue Island, Ill.) operating at 60° C. for approximately one hour to evaporate the solvents.

The solid solvent free iodine/adhesive composition was rolled up and the rolls were fed into the feeder port of a Haake extruder (Thermo Haake USA, Newington, N.H.) with a 1.9 cm (¾-inch) diameter screw at a screw revolutions per minute (RPM) speed of 45. Zones 1,2, and 3 temperatures were set at 121° C., 135° C., and 149° C. with the die temperature also set at 149° C.

The exudate was uniformly red colored, did not show any evidence of gels, and coated smoothly onto a 50-micron thickness polyester film. No evidence of iodine volatilization such as odors or out gassing from the die was apparent. The resulting adhesive exhibited good finger tack.

Example 73

For this example the adhesive was compounded with a complexing agent (PVP/VA copolymer) and iodine/sodium iodide in solvent. Alternatively, these components could be added to a hot melt mixer by a solvent free process.

The base adhesive polymer was 2081 gm of an adhesive consisting of a 70/15/15 iso-octylacrylate/acrylic acid/ethyleneoxide acrylate composition (as described by PCT WO84/03837 Example 14) as a 50% solids solution in 75/25-ethyl acetate/isopropanol.

In a separate container, 230 gm of ethanol, 166.7 gm PVP/VA E-335 (a 30/70 vinylpyrrolidone/vinyl acetate copolymer made by International Specialty Products, Wayne, N.J.), 23 gm iodine, and 27.6 gm sodium iodide were shaken until dissolved and then added to the base adhesive polymer with stirring. After a consistent, uniform coloration was achieved, the iodine/adhesive solution was poured onto silicone liners and the solvents were evaporated as in Example 72.

Similar extrusion conditions were used and a uniformly colored exudate, without gels, was coated onto polyester. No iodine instabilities as evidenced by odors or out gassing were noted. The coated adhesive was quite tacky to the touch.

Example 74

For this example the adhesive was compounded with a complexing agent (2-pyrrolidone/1-ethenylhexadecyl copolymer) and iodine/sodium iodide in solvent. Alternatively, these components could be added to a hot melt mixer by a solvent free process.

2138 gm of a base adhesive polymer blend, a 50/50 mixture of Kraton 1112/Exxon 1310 (mixture components commercially available from Kraton Polymers, Houston, Tex./Exxon Chemical Company, Houston, Tex., respectively) was dissolved as a 30.6% solids toluene solution. The Kraton 1112 resin and Exxon 1310 resin were dissolved in the toluene by placing the container containing the components on a roller mill for six hours.

In a separate container, 22.2 gm iodine, 26.6 gm sodium iodide, 220 gm methylethyl ketone, and 435 gm of 2-pyrrolidone/1-ethenylhexadecyl copolymer (commercially available as Ganex V-216 from International Specialty Products, Wayne, N.J.) were stirred together until the iodine and iodide dissolved. The iodine solution was added to the adhesive base polymer blend with stirring.

Evaporation of the solvents and extrusion of the solid iodine/adhesive composition was conducted as in Example 72. The exudate exhibited good melt uniformity and was consistent in coloration. Again, no evidence of iodine instability attributed to the hot melt coating process was noted.

Examples 75-77

Adhesive compositions containing different levels of 2EHA and NVP were prepared. First two adhesive polymers (M-N) were created as described in Examples 1-4 having the compositions shown in Table 17.

TABLE 17

Composition of Adhesive Polymers M and N

| Adhesive Polymer | 2EHA Amount (g) ((percent)) | NVP Amount (g) ((percent)) | IRG 651 Amount (g) ((percent)) | IOTG Amount (g) ((percent)) | IRG 1076 Amount (g) ((percent)) |
|---|---|---|---|---|---|
| M | 6129.000 (90.000) | 681.000 (10.000) | 10.215 (0.150) | 0.204 (0.003) | 27.240 (0.400) |
| N | 6469.500 (95.000) | 340.500 (5.000) | 10.215 (0.150) | 0.204 (0.003) | 27.240 (0.400) |

Adequate amounts of each of these adhesive polymers M and N were mixed first with 2.5 grams NaI in a small amount of water and then with 2 grams of $I_2$ powder in the Brabender mixer described in Examples 1-4 at 160° C. for 10 minutes. The compositions are shown in Table 18. The compositions were evaluated for homogeneity of the compounded adhesive. A no means that the compounded adhesive cannot pass through an 80-mesh filter. A yes means that the compounded adhesive can pass through an 80-mesh filter.

Comparison Example 2

Adhesive Polymer M was compounded with NaI crystals and $I_2$ powder in the Brabender mixer described in Examples 1-4 at 140° C. to 170° C. for 10, 20, and 30 minutes. The composition and evaluation for homogeneity is shown in Table 18.

TABLE 18

Compositions of Examples 75-77 and Comparison Example 2 and the Homogeneity of the Compositions

| Example Number | Adhesive Polymers from Table 17 Polymer | Amount (g) | NaI Amount (g) | Water Amount (g) | $I_2$ Amount (g) | Homogeneity (Yes or no) |
|---|---|---|---|---|---|---|
| C2 | M | 100.0 | 2.5 | 0.0 | 2.0 | No |
| 75 | M | 100.0 | 2.5 | 1.0 | 2.0 | Yes |
| 76 | M | 100.0 | 2.5 | 1.4 | 2.0 | Yes |
| 77 | N | 100.0 | 2.5 | 1.4 | 2.0 | Yes |

When the compounded adhesives, which were not homogeneous, were coated using the Haake extruder described for Examples 35-42there was a problem of blocking the filter web in the extruder. Adding a small amount of water to sodium iodide to dissolve it solved the problem and then the salt solution or paste could be added to Brabender mixer and/or the Haake extruder to compound with the adhesive compositions. The water evaporated upon compounding at high temperature. Surprisingly, the mixing quality was very good and the dispersion of sodium iodide was much more homogeneous. As little as 100 ml of water could dissolve at least 184 g sodium iodide at 25° C. and at least 302 g when the water was hot. A salt paste could also be prepared if more sodium iodide was added.

Examples 78-85

Stretch release properties were achieved by blending adhesives from Examples 76 and 77 with PHE 3040 in a BRABENDER mixer as described for Examples 1-4 at 150° C. to 160° C. for 8 to 10 minutes. The resulting mixture was hot melt coated between two release liners at 150° C. using a HAAKE single screw extruder as described for Examples 35-42 equipped with a draw die. One of the release liners was the siliconized PET film described for Examples 1-4 and the other release liner was the silicon release liner described for Examples 35-42.

The compositions and coating thickness are shown in Table 19.

TABLE 19

Composition and Coating Thickness of Examples 78-85.

| Example Number | Compounded Adhesive Example Number | Amount (parts) | PHE3040 Amount (parts) | Coating Thickness (microns) |
|---|---|---|---|---|
| 78 | 76 | 90 | 10 | 50 |
| 79 | 76 | 90 | 10 | 125 |
| 80 | 76 | 80 | 20 | 50 |
| 81 | 76 | 80 | 20 | 125 |
| 82 | 77 | 90 | 10 | 50 |
| 83 | 77 | 90 | 10 | 125 |
| 84 | 77 | 80 | 20 | 50 |
| 85 | 77 | 80 | 20 | 125 |

Tensile Test

The tensile test was done according to ASTM test method D 882-97 "Standard Test Method for Tensile Properties of Thin Plastic Sheeting" using an INSTRON materials tester (commercially available from Instron, Canton, Mass.) at a crosshead speed of 30 centimeters/minute (12 inches/minute). The results of this test gave the values for "Yield Strength" in pounds per inch, "Tensile Strength" in pounds per inch, and "Percent Elongation at Break". Pounds per square inch was converted to MegaPascals (MPa). The results of the Tensile Test are shown in Table 20. Examples 76, 79, and 81 are the average of two samples and Examples 77, 83, and 85 are an average of three samples.

TABLE 20

Results of Tensile Test for Examples 76, 77, 79, 81, 83, and 85.

| Example Number | Tensile Yield Stress (MPa) | Elongation at Break (Percent) | Tensile Strength (MPa) |
|---|---|---|---|
| 76 (Control) | 0.193 | 1100 | 0.248 |
| 77 (Control) | 0.110 | 500 | 0.152 |
| 79 | 0.690 | 670 | 1.586 |
| 81 | 1.241 | 610 | 3.034 |
| 83 | 0.483 | 700 | 0.710 |
| 85 | 1.103 | 500 | 2.000 |

The addition of PHE 3040 microfiber dramatically enhanced the tensile strength of the extruded adhesives. In fact some of the reinforced adhesives Examples 79, 81, and 85) were 10 times stronger that the adhesive without the microfiber (Examples 76 and 77). Adhesives with relatively low yield stress, high percent elongation and high tensile strength had the ability to by stretch releasable without breaking.

Stretch Release Test Method

One release liner was removed from the compounded and extruded adhesives from Examples 78-85. The adhesives were laminated onto three different backings: Backing A: polyether polyester (commercially available as Hytrel™ polyester elastomer from Du Pont Co., Wilmington, Del.); Backing B: styrene-ethylene-co-butylene-styrene triblock copolymer (commercially available as Kraton G 1652 from Kraton Polymers Inc., Houston, Tex.); and Backing C: styrene-isoprene-styrene tri-block copolymer (commercially available as Kraton D 1107 from Kraton Polymers Inc.). Next the second release liner was removed for testing for stretch release. Adhesive-laminated strips and compounded and extruded adhesives (Examples 78-85) with one release liner removed were equilibrated at constant temperature (21° C.) and humidity (50% relative humidity) for at least 24 hours and were adhered to a polypropylene (PP) substrate panel by passing a 2 kilogram roller over the strip once. The second release liner was removed from the compounded and extruded adhesives (Examples 78-85). These adhesives were tested without a film backing. The bonded assemblies were allowed to dwell at room temperature for one minute. The assemblies were tested for stretch release by pulling at an angle of between 15 and 35 degrees using an IMASS slip/peel tester (Model 3 M90, commercially available from Instrumentors Inc., Strongsville, Ohio) at a crosshead speed of 30 centimeters/minute (12 inches/minute). The stretch release force was measured in oz/in and converted to N/m. The results are reported in Table 21.

TABLE 21

Stretch Release Testing Results on Examples 78-85 without Backing and Laminated to 3 Different Backings.

| | Laminated Backing Film | | | |
|---|---|---|---|---|
| Adhesive Example Number | A Stretch Release Force (N/m) | B Stretch Release Force (N/m) | C Stretch Release Force (N/m) | No Film Stretch Release Force (N/m) |
| 78 | 424 | 274 | 230 | 118 |
| 79 | 396 | 294 | 219 | 201 |
| 80 | 404 | 250 | 151 | 143 |
| 81 | 402 | 282 | 268 | 270 |
| 82 | 364 | 199 | 108 | 89 |
| 83 | 368 | 244 | 200 | 182 |
| 84 | 363 | 262 | 166 | 135 |
| 85 | 447 | 321 | 322 | 230 |

The stiffness of film backing dramatically affected the stretch release force, which increased with the stiffness of film backing. The thickness of the adhesive film and the microfiber loading did not appear to increase the stretch release force when a film backing was laminated to the compounded adhesive, but the stretch release force increased with increasing thickness of the compounded adhesive or the microfiber loading if the compounded adhesive was not laminated to a film backing.

Probe Tack Test

Probe tack measurements were made following the test method described in ASTMD D 2979-95 using a TA-XY2 texture tester (commercially available from Stable Microsystems, Surrey, U.K.) The results are shown in from Table 22.

TABLE 22

Probe Tack Test Results for Examples 76-85.

| Example Number | Probe Tack Force (g) |
|---|---|
| 76 (Control) | 294 |
| 77 (Control) | 250 |
| 78 | 261 |
| 79 | 429 |
| 80 | 228 |
| 81 | 420 |
| 82 | 250 |
| 83 | 376 |
| 84 | 278 |
| 85 | 441 |

The results in Table 22 showed that the probe tack force was still very well maintained when 10 to 20% of PHE 3040 microfiber was blended with the adhesive. However, it should be emphasized that further increasing microfiber loading did lead to a decrease in the probe tack force, so we typically control the microfiber loading from 5 to 20%.

Unless otherwise indicated, the disclosures of the above cited patents and patent applications are expressly incorporated herein by reference. All parts and percentages are by weight, and all molecular weights are number average molecular weights.

The embodiments described herein are illustrative in nature and not intended to limit the scope of the invention. One skilled in the art will recognize that variations are possible without departing from the spirit or scope of the invention.

The invention claimed is:

1. The hot melt coatable adhesive comprising
solubilized iodine,
solubilized iodide,
a preadhesive composition, and
a non-volatile solubilizing liquid;
wherein the solubilizing liquid is selected from the group consisting of glycols, 3-methoxy-methylbutanol, polyethoxylated phenols, alkyl, aryl, and aralkyl ether glycols, polyethoxylated alkyl phenols, mono or polysubstituted polyethylene glycols, alkyl substituted N-alkyl pyrrolidones, N-butylbenzene sulfonamide, benzoate esters, polyethylene glycols, ethylene oxide propylene oxide random and block copolymers having a molecular weight less than 10,000 daltons, polypropylene glycol, polytetramethylene glycol, random and block copolymers of C2-C4 alkylene oxide groups, and a polymerizable solubilizing liquid.

2. The hot melt adhesive of claim 1, wherein the solubilizing liquid is polymerizable.

3. The hot melt adhesive of claim 1, wherein the solublizing liquid is an iodine/iodide complexing agent.

4. The hot melt adhesive of claim 3, wherein the iodine/iodide complexing agent comprises a compound capable of forming iodophors selected from the group consisting of compounds containing hydroxyl functionalities, compounds containing lactam functionality, compounds containing amide functional groups, compounds containing amine oxide functional groups, and compounds containing polyether functionality.

5. The hot melt adhesive of claim 1, wherein the solubilizing liquid is present in sufficient amount to solubilize the iodine and iodide such that there are no insoluble particles of a substantial size to interfere with a hot melt coating process.

6. The hot melt adhesive of claim 1, wherein the solublizing liquid is a single liquid.

7. The hot melt adhesive of claim 1, further comprising an antimicrobial agent in addition to iodine.

8. The hot melt adhesive of claim 1, wherein the preadhesive composition is selected from the group consisting of natural rubbers, synthetic rubbers, styrene block copolymers, polyvinyl ethers, poly (meth)acrylates, and polyolefins.

9. The hot melt adhesive of claim 8, wherein the polyolefins are selected from the group consisting of polyalpha olefins, silicones, and blends or mixtures thereof.

10. The hot melt adhesive of claim 8, wherein the poly (meth)acrylates further comprise other vinylic non-acrylate monomers.

11. The hot melt adhesive claim 8, wherein the styrene block copolymers are selected from the group consisting of styrene-isoprene-styrene (SIS), styrene-butadiene, styrene-isoprene and derivatives thereof.

12. The hot melt adhesive of claim 10, wherein the vinylic monomers are selected from the group consisting of N-vinyl lactams, (meth)acrylamides, styrene, methylvinyl ether, polystyrene macromers, and vinyl acetate.

13. The hot melt coatable adhesive of claim 1 disposed within a melt processable packaging material.

14. The hot melt coatable adhesive of claim 1 wherein the adhesive is a pressure sensitive adhesive.

15. The hot melt coatable adhesive of claim 14, further comprising a fibrous reinforcing material.

16. The hot melt coatable adhesive of claim 14, wherein the reinforcing material is a semicrystalline polymer distributed in the adhesive and immiscible in the adhesive composition.

17. The hot melt coatable adhesive of claim 14, wherein the reinforcing material is in the form of substantially spherical particles having an average diameter less than about 20 micrometers.

18. An adhesive composite, comprising a substrate and the hot melt adhesive of claim 1.

19. The adhesive composite of claim 18, wherein the composite is a surgical incise drape.

20. The adhesive composite of claim 18, wherein the adhesive coated substrate has antimicrobial efficacy at 120 min. as measured by the Direct Inoculation Assay.

21. The adhesive composite of claim 18, wherein the adhesive coated substrate has antimicrobial efficacy at 60 min. as measured by the Direct Inoculation Assay.

22. The adhesive composite of claim 18, wherein the adhesive coated substrate has antimicrobial efficacy at 30 min. as measured by the Direct Inoculation Assay.

* * * * *